United States Patent
Cyko et al.

(12)

(10) Patent No.: US 11,304,826 B1
(45) Date of Patent: Apr. 19, 2022

(54) TIBIAL TRIALS WITH SLIDING SPACERS AND METHOD

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Christopher Cyko, Bartlett, TN (US); Jason S. Jordan, Hernando, MS (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 0 days.

(21) Appl. No.: 16/784,724

(22) Filed: Feb. 7, 2020

Related U.S. Application Data

(60) Provisional application No. 62/804,444, filed on Feb. 12, 2019.

(51) Int. Cl.
*A61F 2/46* (2006.01)
*A61F 2/38* (2006.01)
*A61F 2/30* (2006.01)

(52) U.S. Cl.
CPC ........ *A61F 2/4684* (2013.01); *A61F 2/30724* (2013.01); *A61F 2/3859* (2013.01); *A61F 2/3868* (2013.01)

(58) Field of Classification Search
CPC ...... A61F 2/4684; A61F 2/389; A61F 2/3859; A61F 2/3886; A61F 2/02; A61F 2/461; A61F 2002/4205; A61F 2/30724; A61F 2/3868
See application file for complete search history.

(56) References Cited

U.S. PATENT DOCUMENTS

| | | | | |
|---|---|---|---|---|
| 5,702,464 A | * | 12/1997 | Lackey | A61F 2/4684 623/20.32 |
| 5,782,925 A | * | 7/1998 | Collazo | A61F 2/4684 623/20.28 |
| 5,964,808 A | * | 10/1999 | Blaha | A61F 2/3868 623/20.28 |
| 8,603,101 B2 | | 12/2013 | Claypool et al. | |
| 9,763,807 B2 | | 9/2017 | Claypool et al. | |
| 11,207,198 B2 | * | 12/2021 | Oh | A61F 2/38 |
| 2004/0225368 A1 | * | 11/2004 | Plumet | A61F 2/3886 623/20.15 |
| 2008/0051908 A1 | * | 2/2008 | Angibaud | A61F 2/389 623/20.32 |
| 2008/0243263 A1 | * | 10/2008 | Lee | A61F 2/3868 623/20.29 |
| 2010/0191342 A1 | * | 7/2010 | Byrd | A61F 2/08 623/20.28 |

(Continued)

*Primary Examiner* — Ann Schillinger
(74) *Attorney, Agent, or Firm* — Kacvinsky Daisak Bluni PLLC

(57) ABSTRACT

Embodiments of the invention include a knee arthroplasty trialing system and method with a femoral component and a tibial trial that has one or more spacers and one or more articular trials. Some embodiments include spacers and articular trials that may be moved in and out of the joint space without significantly distracting the femoral component away from the tibial trial. Some spacers and trials are configured to be inserted and removed from a joint space substantially along an anterior-posterior axis.

20 Claims, 19 Drawing Sheets

(56) References Cited

U.S. PATENT DOCUMENTS

| | | | | |
|---|---|---|---|---|
| 2010/0305709 | A1* | 12/2010 | Metzger | A61F 2/3868 623/20.27 |
| 2011/0251694 | A1* | 10/2011 | Wasielewski | A61F 2/38 623/20.15 |
| 2012/0101585 | A1* | 4/2012 | Parisi | A61F 2/3886 623/20.32 |
| 2012/0158152 | A1* | 6/2012 | Claypool | A61F 2/3868 623/20.33 |
| 2013/0006371 | A1* | 1/2013 | Wogoman | A61F 2/461 623/20.21 |
| 2013/0261504 | A1* | 10/2013 | Claypool | A61B 5/1036 600/587 |
| 2019/0298543 | A1* | 10/2019 | Hashida | A61B 17/1675 |

\* cited by examiner

TIBIAL TRIALS WITH SLIDING SPACERS AND METHOD

CROSS-REFERENCE TO RELATED APPLICATIONS

This is a non-provisional of, and claims the benefit of the filing date of, U.S. provisional patent application No. 62/804,444, filed Feb. 12, 2019, entitled "Tibial Trials with Sliding Spacers and Method," which application is incorporated by reference herein in its entirety.

FIELD OF THE INVENTION

The present invention relates generally to the field of medical instruments, and more particularly relates to a tibial trial and method that may be used in conjunction with a femoral implant or trial to determine an appropriate size for implant components of a knee arthroplasty device. More particularly, the tibial trial includes one or more spacers that slide into position in a manner that reduces distraction of a knee joint during trialing.

BACKGROUND

Knee replacement or arthroplasty is a surgical procedure in which portions of a patient's knee are removed and replaced with a knee arthroplasty device or implant (e.g., portions, sections, or the like of a patient's distal femur and a proximal tibia are replaced with an implanted orthopedic arthroplasty device or implant). For example, total knee replacement may involve removal and replacement of the entire knee joint.

During knee replacement surgeries, trial components are commonly used to size and/or test the fit and alignment of a knee arthroplasty device relative to a bone that was reshaped by a surgeon prior to implantation of the actual knee arthroplasty device. For example, in the course of positioning and sizing femoral and tibial implant components of a knee arthroplasty device, it is common to simulate final sizing with trial devices or "trials" or "provisional devices" that are placed temporarily while knee mobility checks are accomplished. The trials are removed and replaced with implantable components to form the final, implantable arthroplasty device or implant. The trials may include a femoral articulating trial, a tibia modular baseplate trial, and a tibia modular articulating trial. The tibia modular articulating trial (whether as a single component or multiple components) will typically be offered in a plurality of sizes and thicknesses which interact with a single thickness modular tibia baseplate trial. The combined trials typically simulate the final geometry of the implant. The tibia modular articulating trial must interact appropriately in size and shape with the femoral articulating trial and the final femoral component, and with the modular baseplate trial and the final tibial tray component. The tibia modular articulating trials therefore must function both during intermediate trailing steps and in interactions with final implant components.

With prior art devices, this duality of interaction has led to at least two challenges with trials, and especially tibial trials. A first challenge is the number of trial variants needed to accommodate different articular geometries that mate with like size and shaped modular baseplates, each of which interacts in a differing way with like femoral components. A second challenge to be overcome are trial geometries that can make the trials difficult to insert and remove from a joint space while pluralities of thicknesses are being evaluated.

What is needed are improved tibial trials that provide for appropriately sized and shaped components during all steps of trialing and that are more easily inserted and removed during the trialing process. It is with this in mind that the present disclosure is presented.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

An embodiment of the invention is a tibial trial that includes at least a tibial tray, a spacer, and an articular trial. The spacer may include a superior side and an inferior side. The inferior side of some embodiments is sized and shaped to connect with at least a portion of the tibial tray to restrict motion of the spacer relative to the tibial tray when connected to the tibial tray. The articular trial may have an inferior side and a superior side. Embodiments of the superior side are configured to interact with a femoral trial or a femoral implant. The articular trial may be configured to be slid in a substantially anterior to posterior direction between the spacer and the femoral trial or the femoral implant. When the articular trial is slid in a substantially anterior to posterior direction between the spacer and the femoral trial or the femoral implant, the inferior side of the articular trial interlocks with the superior side of the spacer without significantly moving the femoral trial or femoral implant superiorly relative to the spacer.

In one embodiment, the tibial tray is a trial, not configured and composed for permanent implantation.

In one embodiment, the tibial tray includes at least a partial indentation sized and shaped to receive a portion of the spacer.

In one embodiment, the at least a partial indentation is formed by a rim about a substantial portion of a perimeter of the tibial tray.

In one embodiment, a portion of the inferior side of the spacer substantially fits within the rim on the tibial tray when the inferior side of the spacer is connected to the tibial tray.

In one embodiment, the tibial tray includes a ridge across a superior portion of the tibial tray.

In one embodiment, a length of the ridge is in a substantially anterior-posterior direction.

In one embodiment, the ridge is substantially centrally located on the tibial tray.

In one embodiment, the spacer includes a notch on its inferior side to receive the ridge of the tibial tray.

In one embodiment, the superior side of the articular trial includes a post to provide posterior stabilization between the articular trial and the femoral trial or femoral implant.

In one embodiment, the articular trial is slid substantially in an anterior to posterior direction relative to the spacer, the inferior side of the articular trial interlocks with the superior side of the spacer such that medial and lateral movement between the articular trial and the spacer are restricted.

In one embodiment, when the articular trial is slid substantially in an anterior to posterior direction relative to the spacer, the inferior side of the articular trial interlocks with the superior side of the spacer such that inferior and superior movement between the articular trial and the spacer are restricted.

In one embodiment, when the articular trial is slid substantially in an anterior to posterior direction relative to the spacer, the inferior side of the articular trial interlocks with the superior side of the spacer such that anterior movement between the articular trial and the spacer is stopped at a predefined limit.

In one embodiment, after the articular trial has been slid between the spacer and the femoral trial or the femoral implant to a point where the inferior side of the spacer is connected to the tibial tray and the inferior side of the articular trial is interlocked with the articular trial, the combined spacer and articular trial may be first lifted from the tibial tray by the articular trial and then moved anteriorly out from between the tibial tray and the femoral trial or the femoral implant.

Another embodiment of the invention is a tibial trial that includes a tibial tray, a spacer, and an articular trial. The tibial tray may include a bone-engaging inferior surface and may have a superior surface. The spacer may have a superior side with a first interlocking mechanism and an inferior side. The inferior side of some embodiments is connectable with at least a portion of the tibial tray to restrict motion of the spacer relative to the tibial tray when connected to the tibial tray. The articular trial may have an inferior side with a second interlocking mechanism configured to engage with the first interlocking mechanism. The articular trial may also include a superior side configured to interact with a femoral trial or a femoral implant. In some embodiments, the first interlocking mechanism includes a first surface in an inferior-superior plane, and the second interlocking mechanism includes a second surface in an inferior-superior plane that is engageable with the first surface to restrict movement of the spacer relative to the articular trial in a first direction. The first interlocking mechanism may include a first stop oblique to the first surface, and the second interlocking mechanism may include a second stop oblique to the second surface that is engageable with the first stop to limit movement of the articular trial relative to the spacer along the first surface.

In one embodiment, the tibial tray is a trial, not configured and composed for permanent implantation.

In one embodiment, the tibial tray includes at least a partial indentation sized and shaped to receive a portion of the spacer.

In one embodiment, the at least a partial indentation is formed by a rim about a substantial portion of a perimeter of the tibial tray.

In one embodiment, a portion of the inferior side of the spacer substantially fits within the rim on the tibial tray when the inferior side of the spacer is connected to the tibial tray.

In one embodiment, the tibial tray includes a ridge across the superior surface of the tibial tray.

In one embodiment, a length of the ridge is in a substantially anterior-posterior direction.

In one embodiment, the ridge is substantially centrally located on the tibial tray.

In one embodiment, the spacer includes a notch on its inferior side to receive the ridge of the tibial tray.

In one embodiment, the superior side of the articular trial includes a post to provide posterior stabilization between the articular trial and the femoral trial or femoral implant.

In one embodiment, the first surface in an inferior-superior plane of the first interlocking mechanism is oriented substantially in an anterior-posterior direction; and wherein the second surface in an inferior-superior plane of the second interlocking mechanism is oriented substantially in an anterior-posterior direction.

In one embodiment, the first interlocking mechanism includes a first hook to engage with the second interlocking mechanism to restrict inferior and superior movement between the articular trial and the spacer.

In one embodiment, the second interlocking mechanism includes a second hook to engage with the first interlocking mechanism to restrict inferior and superior movement between the articular trial and the spacer.

In one embodiment, the first interlocking mechanism includes a first hook to engage with a second hook of the second interlocking mechanism to restrict inferior and superior movement between the articular trial and the spacer.

In one embodiment, after the first interlocking mechanism is engaged with the second interlocking mechanism, the combined spacer and articular trial may be lifted from the tibial tray and then moved anteriorly out from between the tibial tray and the femoral trial or the femoral implant.

Yet another embodiment of the invention is a knee arthroplasty trialing system that includes at least a femoral component and a tibial trial. Embodiments of the tibial trial include a tibial tray, a first spacer, and an articular trial. The tibial tray may include a bone-engaging inferior surface and a superior surface. The first spacer may include a superior side having a first interlocking mechanism and an inferior side. The inferior side of some embodiments is connectable with at least a portion of the tibial tray to restrict motion of the first spacer relative to the tibial tray when connected to the tibial tray. The articular trial may include an inferior side having a second interlocking mechanism configured to engage with the first interlocking mechanism and a superior side configured to interact with a femoral trial or a femoral implant. The first interlocking mechanism may include a first surface in an inferior-superior plane, and the second interlocking mechanism may include a second surface in an inferior-superior plane that is engageable with the first surface to restrict movement of the first spacer relative to the articular trial in a first direction. The first interlocking mechanism includes a first stop oblique to the first surface, and the second interlocking mechanism includes a second stop oblique to the second surface that is engageable with the first stop to limit movement of the articular trial relative to the first spacer along the first surface.

In one embodiment, the system is for performing a total knee arthroplasty.

In one embodiment, the femoral component is a femoral trial.

In one embodiment, the femoral component is a femoral implant.

In one embodiment, the tibial tray is a trial, not configured and composed for permanent implantation.

In one embodiment, the tibial tray includes at least a partial indentation sized and shaped to receive a portion of the first spacer.

In one embodiment, the at least a partial indentation is formed by a rim about a substantial portion of a perimeter of the tibial tray.

In one embodiment, a portion of the inferior side of the first spacer substantially fits within the rim on the tibial tray when the inferior side of the first spacer is connected to the tibial tray.

In one embodiment, the tibial tray includes a ridge across the superior surface of the tibial tray.

In one embodiment, a length of the ridge is in a substantially anterior-posterior direction.

In one embodiment, the ridge is substantially centrally located on the tibial tray.

In one embodiment, the first spacer includes a notch on its inferior side to receive the ridge of the tibial tray.

In one embodiment, the superior side of the articular trial includes a post to provide posterior stabilization between the articular trial and the femoral trial or femoral implant.

In one embodiment, the first surface in an inferior-superior plane of the first interlocking mechanism is oriented substantially in an anterior-posterior direction; and wherein the second surface in an inferior-superior plane of the second interlocking mechanism is oriented substantially in an anterior-posterior direction.

In one embodiment, the first interlocking mechanism includes a first hook to engage with the second interlocking mechanism to restrict inferior and superior movement between the articular trial and the spacer.

In one embodiment, the second interlocking mechanism includes a second hook to engage with the first interlocking mechanism to restrict inferior and superior movement between the articular trial and the spacer.

In one embodiment, the first interlocking mechanism includes a first hook to engage with a second hook of the second interlocking mechanism to restrict inferior and superior movement between the articular trial and the spacer.

In one embodiment, after the first interlocking mechanism is engaged with the second interlocking mechanism, the combined spacer and articular trial may be lifted from the tibial tray and then moved anteriorly out from between the tibial tray and the femoral trial or the femoral implant.

In one embodiment, the knee arthroplasty trialing system further includes a second spacer with a second thickness that is different from a thickness of the first spacer.

In one embodiment, the second spacer with the second thickness is in operative part thicker than the first spacer.

In one embodiment, the second spacer with the second thickness is in operative part thinner than the first spacer.

Still another embodiment of the invention is a method of determining an appropriate size for a knee arthroplasty device by using trials. Acts of the method may include placing a tibial tray on a patient's tibia, placing a femoral component on the patient's femur, connecting a first spacer with a first thickness to the tibial tray, and inserting an articular trial on a superior side of the first spacer between the first spacer and the femoral component without significantly moving the femoral component superiorly relative to the first spacer. The method may also include assessing joint balance with the first spacer and articular trial connected and inserted. If the assessment is satisfactory, the first spacer and the articular trial are removed and trialing may be complete. If the assessment is not satisfactory, the first spacer and the articular trial may be removed and a second spacer with a second thickness may be connected to the tibial tray. The method may also include inserting the articular trial on a superior side of the second spacer between the second spacer and the femoral component and assessing joint balance with the second spacer and articular trial connected and inserted. The method may additionally include removing the second spacer and the articular trial from between the tibial tray and the femoral component.

In one embodiment, the act of connecting the first spacer to the tibial tray includes moving the first spacer in a substantially anterior to posterior direction.

In one embodiment, the act of connecting the first spacer to the tibial tray includes moving the first spacer in a substantially anterior to posterior direction and in a substantially superior to inferior direction.

In one embodiment, the act of inserting the articular trial on the superior side of the first spacer between the first spacer and the femoral component includes sliding the articular trial substantially anteriorly to posteriorly relative to the first spacer.

In one embodiment, the act of inserting an articular trial on a superior side of the first spacer includes interlocking an inferior side of the articular trial with the superior side of the first spacer.

In one embodiment, the interlocking includes restricting medial and lateral movement between the articular trial and the first spacer.

In one embodiment, the interlocking includes restricting inferior and superior movement between the articular trial and the first spacer.

In one embodiment, the interlocking includes restricting anterior movement between the articular trial and the first spacer at a predefined limit.

In one embodiment, the act of removing the first spacer and the articular trial includes lifting at least part of the first spacer and the articular trial together in a substantially inferior to superior direction.

In one embodiment, connecting the second spacer with the second thickness to the tibial tray includes connecting a second spacer that is in operative part thicker than the first spacer.

In one embodiment, connecting the second spacer with the second thickness to the tibial tray includes connecting a second spacer that is in operative part thinner than the first spacer.

In one embodiment, the act of connecting the second spacer to the tibial tray includes moving the second spacer in a substantially anterior to posterior direction.

In one embodiment, the act of connecting the second spacer to the tibial tray includes moving the second spacer in a substantially anterior to posterior direction and in a substantially superior to inferior direction.

In one embodiment, the act of inserting the articular trial on a superior side of the second spacer between the second spacer and the femoral component includes sliding the articular trial substantially anteriorly to posteriorly relative to the second spacer.

In one embodiment, the act of inserting the articular trial on a superior side of the second spacer between the second spacer and the femoral component includes inserting an articular trial on a superior side of the first spacer between the first spacer and the femoral component without significantly moving the femoral component superiorly relative to the second spacer.

In one embodiment, the act of inserting an articular trial on a superior side of the second spacer includes interlocking an inferior side of the articular trial with the superior side of the second spacer.

In one embodiment, interlocking includes restricting medial and lateral movement between the articular trial and the second spacer.

In one embodiment, interlocking includes restricting inferior and superior movement between the articular trial and the second spacer.

In one embodiment, interlocking includes restricting anterior movement between the articular trial and the second spacer at a predefined limit.

In one embodiment, the act of removing the second spacer and the articular trial includes lifting at least part of the second spacer and the articular trial together in a substantially inferior to superior direction.

Figure 1:
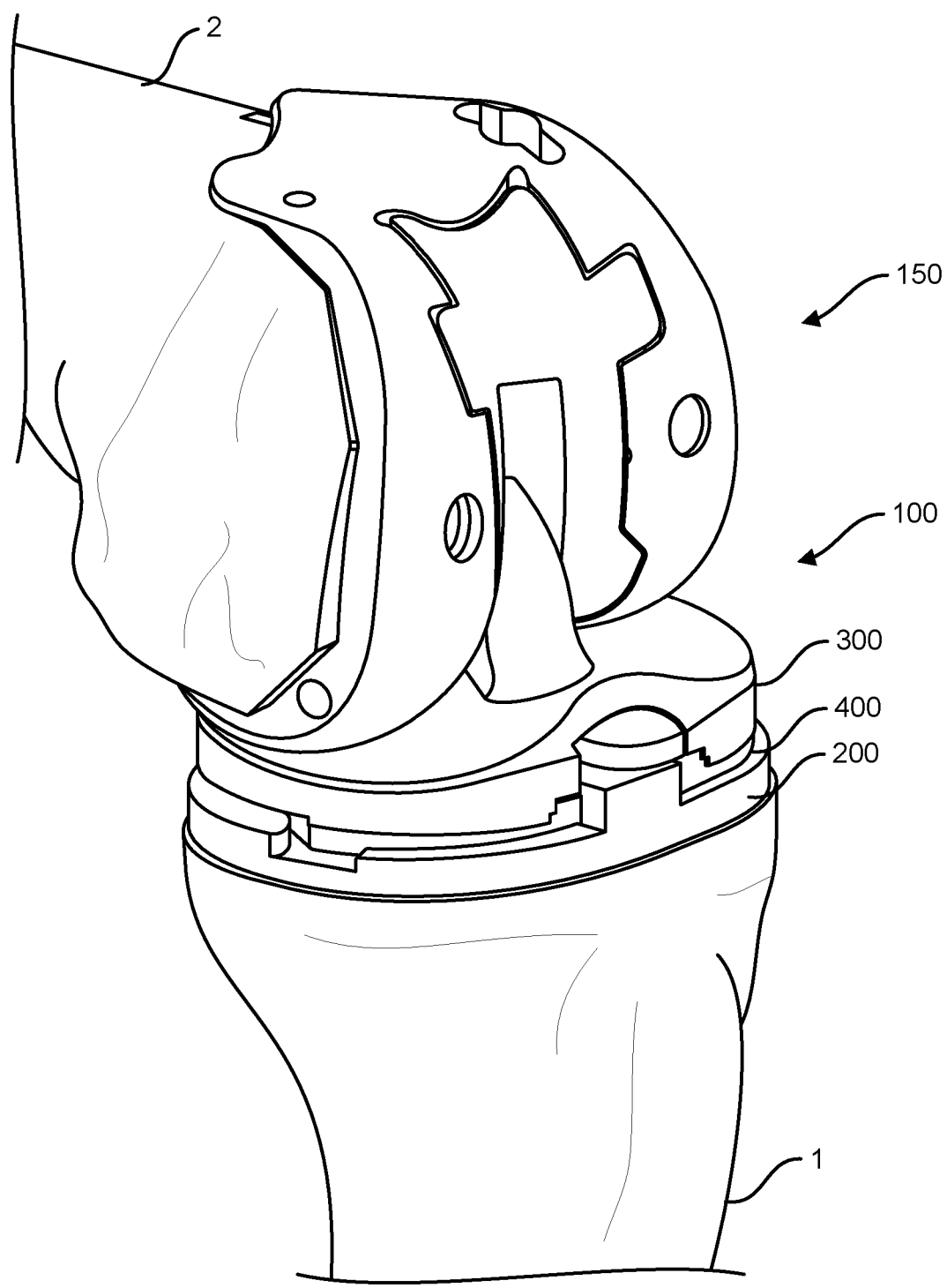
FIG. 1 is a perspective view of an example embodiment of femoral and tibial trials used in a total knee arthroplasty, the femoral and tibial trials being shown in place on a patient's femur and a patient's tibia.
Figure 2:
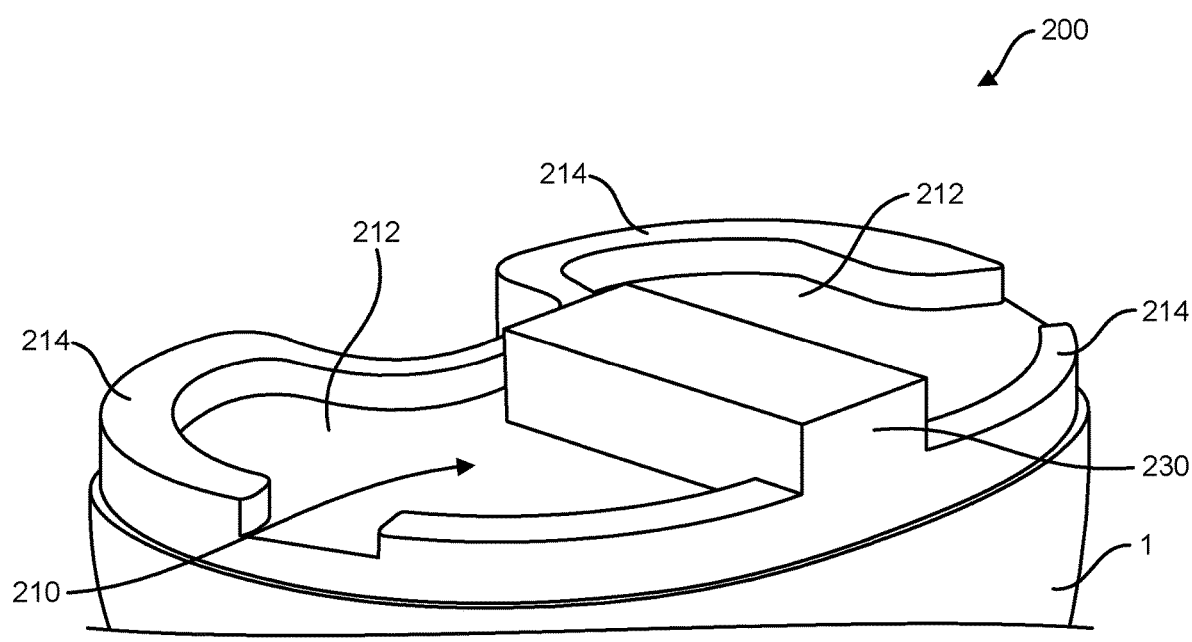
FIG. 2 is a perspective view of an example of an embodiment of a tibial tray trial shown in FIG. 1 in accordance with one or more aspects of the present disclosure, the tibial tray trial being shown in place on the patient's tibia.

The drawings are not necessarily to scale. The drawings are merely representations, not intended to portray specific parameters of the disclosure. The drawings are intended to depict exemplary embodiments of the disclosure, and therefore are not be considered as limiting in scope. In the drawings, like numbering represents like elements.

DETAILED DESCRIPTION

Various features, aspects, or the like of a knee arthroplasty trialing system and method will now be described more fully hereinafter with reference to the accompanying drawings, in which one or more aspects of the knee arthroplasty trialing system and/or method will be shown and described. It should be appreciated that the various features, aspects, or the like may be used independently of, or in combination, with each other. It will be appreciated that the knee arthroplasty trialing system and method as disclosed herein may be embodied in many different forms and should not be construed as being limited to the embodiments set forth herein. Rather, these embodiments are provided so that this disclosure will convey certain illustrations of aspects of the knee arthroplasty trialing system and method to those skilled in the art. In the drawings, like numbers refer to like elements throughout unless otherwise noted.

As will be described in greater detail below, a knee arthroplasty trialing system and/or method according to the present disclosure may include one or more features to simplify implantation, installation, or the like (used interchangeably without the intent to limit). For example, in one embodiment, the knee trialing system includes a tibial tray, an articular trial, and one or more interchangeable spacers arranged and configured to be inserted in-between the tibial tray and the articular trial. In use, the one or more interchangeable spacers include one or more features arranged and configured to engage the tibial tray and the articular trial to restrict motion of the spacer relative to the tibial tray and the articular trial when connected thereto. In one embodiment, the articular trial and/or the spacers are arranged and configured to be slid in a substantially anterior to posterior direction relative to the trial tray and/or a femoral trial or a femoral implant.

Referring to FIG. 1, components of a knee arthroplasty trialing system in place on a tibia 1 and a femur 2 are illustrated. As illustrated, the knee arthroplasty trialing system is used as part of a total knee arthroplasty procedure, but in other embodiments a knee arthroplasty trialing system in accordance with the present disclosure may be part of a partial knee arthroplasty procedure, such as but not limited to, a unicompartmental knee arthroplasty procedure. As illustrated, a femoral trial 150 is shown attached, coupled, implanted, installed, etc. (used interchangeably herein without the intent to limit) on the femur 2. Generally speaking, as will be appreciated by one of ordinary skill in the art, a trial is generally not configured and composed for permanent implantation. In other embodiments, a final femoral implant rather than or in addition to a femoral trial may be used while tibial trial components are tried and compared.

Referring to FIGS. 1-14, an example embodiment of a tibial trial 100 and its component parts in accordance with one or more aspects of the present disclosure are shown. The tibial trial 100 shown in FIG. 1 is representative of one embodiment and includes a tibial tray 200, an articular trial 300, and a first spacer 400. As will be shown and described in greater detail, a thicker, second spacer 500 (FIGS. 5A-5D and 12-14) may be used in place of the first spacer 400.

The tibial tray 200 shown in FIGS. 1, 2, and 6-14 includes a bone-engaging inferior surface and a superior surface 210. As illustrated, the example embodiment of the tibial tray 200 is arranged and configured as a trial implant, not configured and composed for permanent implantation. However, other embodiments may use a final, implantable tibial tray in combination with other components of the knee arthroplasty trialing system disclosed. The bone-engaging inferior surface of the tibial tray 200 may include an intramedullary stem or other bone engaging features to provide temporary, secure engagement of the tibial tray 200 with the tibia 1.

Referring to FIGS. 2, 6, 11, and 12, in one embodiment, the superior surface 210 of the tibial tray 200 may include a rim 214 extending about a substantial portion of a perimeter of the tibial tray 200. As shown, the superior surface 210 of the tibial tray 200 may also include an indentation 212 defined partially by the rim 214 extending about the perimeter of the tibial tray 200. As will be shown and described in greater detail, in use, the indentation 212 is sized and shaped to receive at least a portion of the first spacer 400 or the second spacer 500 when either is deployed. Although the tibial tray 200 will be shown and described with an indentation 212 sized and configured to receive the first and/or second spacer 400, 500, it is envisioned that in other embodiments, the tibial tray may include other effective mechanisms for connecting the tibial tray 200 and the first spacer 400 or the second spacer 500 when it is deployed.

As illustrated in the example embodiment, the tibial tray 200 may also include a ridge, a projection, etc. 230 extending from the superior surface 210. As shown, the ridge 230 may extend a majority of the way across the superior surface 210 such as, for example, from an anterior edge of the tibial tray towards a posterior edge of the tibial tray, but in other embodiments, the ridge may extend less of a way across or may extend all the way across the superior surface 210. As illustrated, the longer dimension or length of the ridge 230 extends in a substantially anterior-posterior direction, although such is not necessary. For example, in other embodiments, the ridge may extend in a medial-lateral direction or in an effective oblique direction. The ridge 230 depicted is substantially centrally located medially-laterally on the superior surface 210 of the tibial tray 200, although such is not necessary. For example, in other embodiments, the ridge may be offset from a substantially central location. Alternatively, in some embodiments, the tibial tray may not include any type of ridge structure.

Referring to FIGS. 4A-4D, an example embodiment of the first spacer 400 in accordance with one or more aspects of the present disclosure is shown. As will be described in greater detail below, in use, the first spacer 400 is arranged and configured to couple to the tibial tray 200 and to the articular trial 300. In use, the first spacer 400 spaces the articular trial 300 from the tibial tray 200. In one embodiment, the first spacer 400 is arranged and configured to couple to the tibial tray 200 and to the articular trial 300 in a lateral movement such as, but not limited to, a slidable movement along an anterior-posterior path.

In the illustrated embodiment, the first spacer 400 may include a superior side 410 with a first interlocking mechanism 412 and an inferior side 420. The illustrated inferior side 420 is arranged and configured to be selectively connectable, attached, coupled, or the like with at least a portion of the tibial tray 200 to restrict motion of the first spacer 400 relative to the tibial tray 200 when the first spacer 400 is connected to the tibial tray 200, as shown in FIGS. 1 and 7-9. Specifically, in the illustrated embodiment, the inferior side 420 of the first spacer 400 may include a periphery 422 (FIGS. 4B and 4C) sized and configured to fit within the indention 212 formed in the superior surface 210 of the tibial tray 200, as shown in FIGS. 1 and 7-9. Thus arranged, the periphery 422 formed on the first spacer 400 and the indentation 212 formed in the superior surface 210 of the tibial tray 200 restrict anterior, posterior, medial, and lateral movement of the first spacer 400 relative to the tibial tray 200.

Figure 4A:
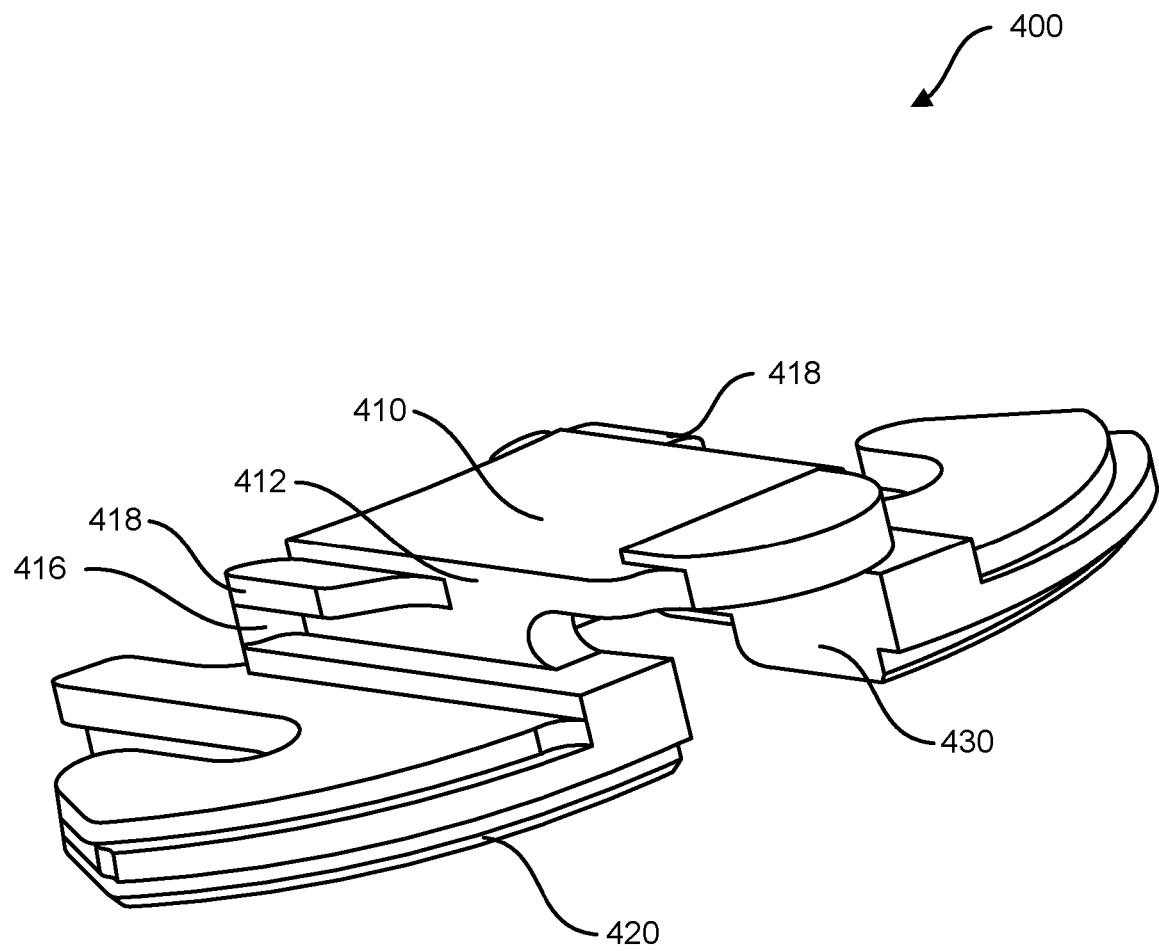
FIG. 4A is perspective view of an example of embodiment of a spacer shown in FIG. 1 in accordance with one or more aspects of the present disclosure.
Figure 4B:
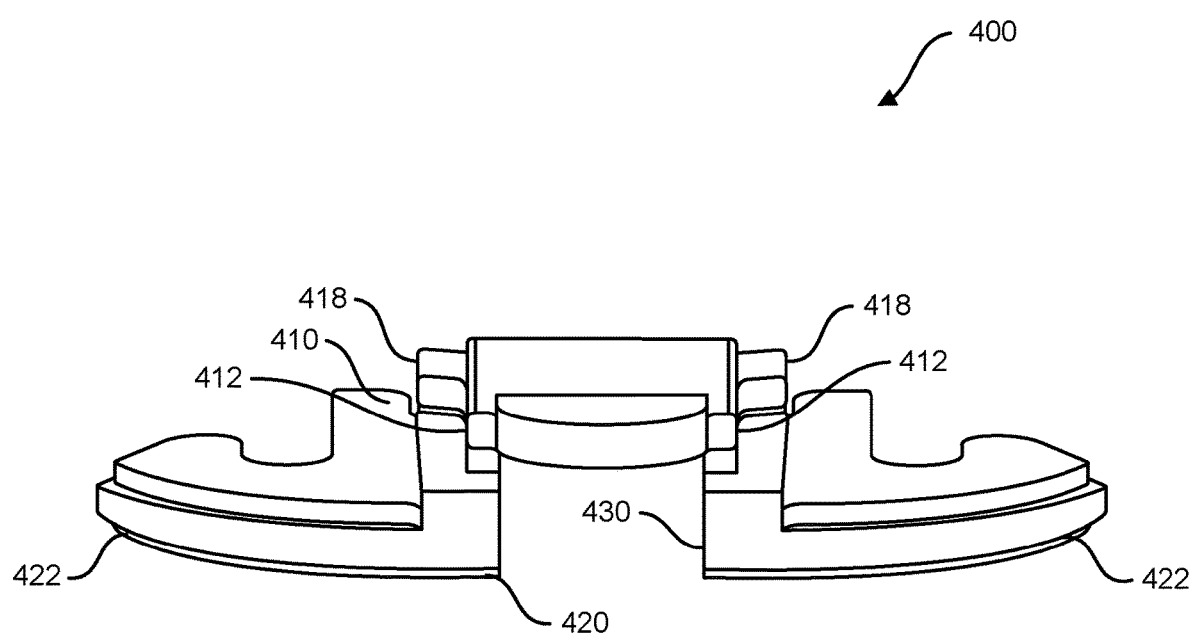
FIG. 4B is an anterior perspective view of the spacer of FIG. 4A showing a portion of the superior side of the spacer.
Figure 4C:
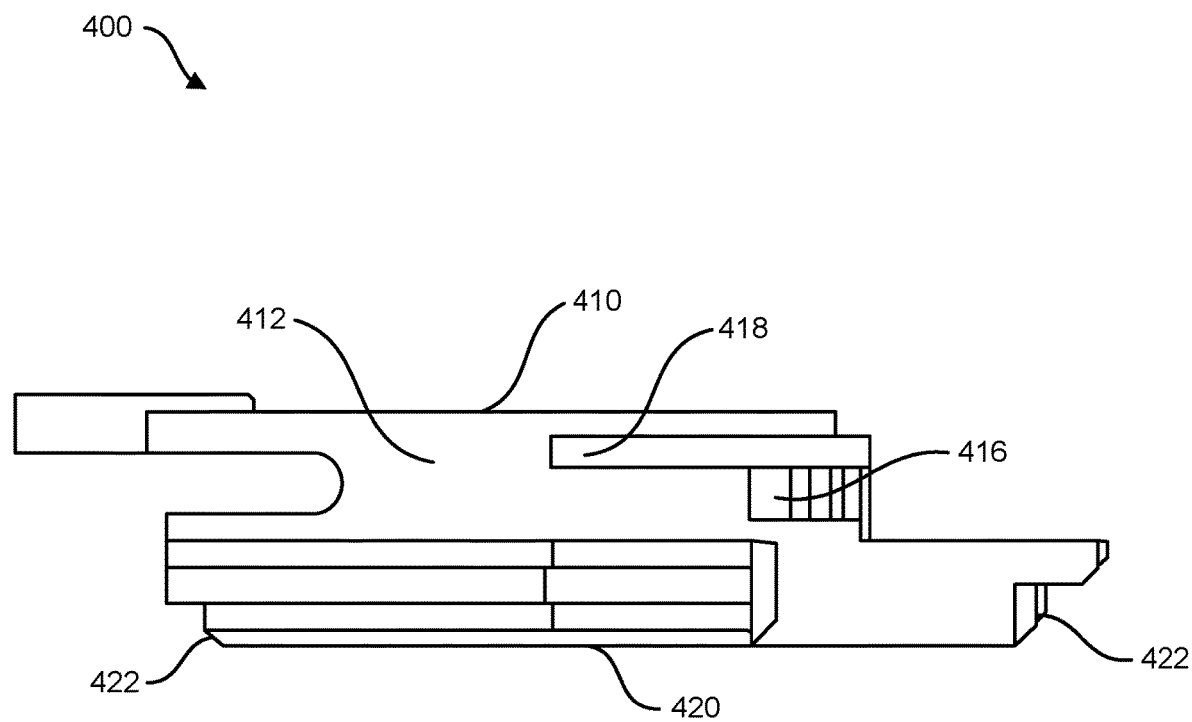
FIG. 4C is a side elevation view of the spacer of FIG. 4A.
Figure 4D:
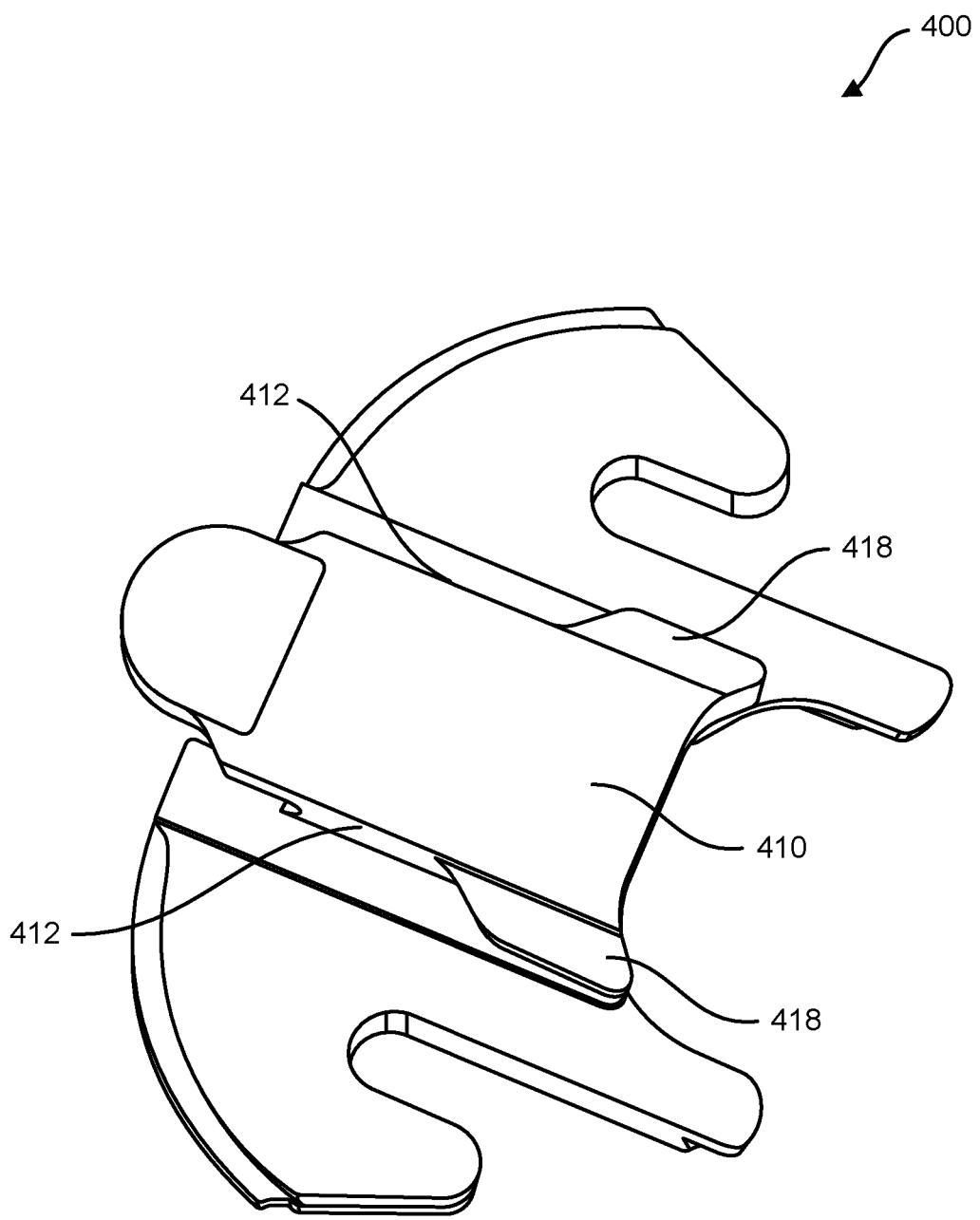
FIG. 4D is a perspective view of the spacer of FIG. 4A showing a superior side of the spacer.

Referring to FIGS. 4A and 4B, the first spacer 400 may also include a notch 430 on the inferior side 420 of the spacer 400. In use, the notch 430 is sized and shaped to receive the ridge 230 extending from the superior surface 210 of the tibial tray 200 when the first spacer 400 is coupled to the tibial tray 200 (FIGS. 1 and 7-9). Thus arranged, the interaction between the notch 430 formed in the first spacer 400 and the ridge 230 formed on the tibial tray 200 restricts medial and lateral movement of the first spacer 400 relative to the tibial tray 200. In other embodiments without a ridge type structure, coupling between elements such as the indention 212 and the ridge 214 of the tibial tray 200 and the periphery 422 of the first spacer 400 may adequately restrict medial and lateral movement of the first spacer 400 relative to the tibial tray 200. Alternatively, it is envisioned that the formation of the interacting notch and ridge may be reversed. For example, the ridge may extend from the first spacer and the notch may be formed in the tibial tray.

As illustrated, in one embodiment, the first interlocking mechanism 412 includes at least a first surface in an inferior-superior plane. The first surface shown is oriented substantially in an anterior-posterior direction, but in other embodiments could be medially-laterally oriented or at some oblique orientation. The first interlocking mechanism 412 shown also includes a first stop 416 oblique to the first surface, as shown best in FIGS. 4A and 4C. The first interlocking mechanism 412 shown also includes a pair of first hooks, projections, laterally-extending ridges, or the like 418 configured to engage with the articular trial 300 and restrict inferior and superior movement between the articular trial and the spacer, as will be described in greater detail below.

Figure 3A:
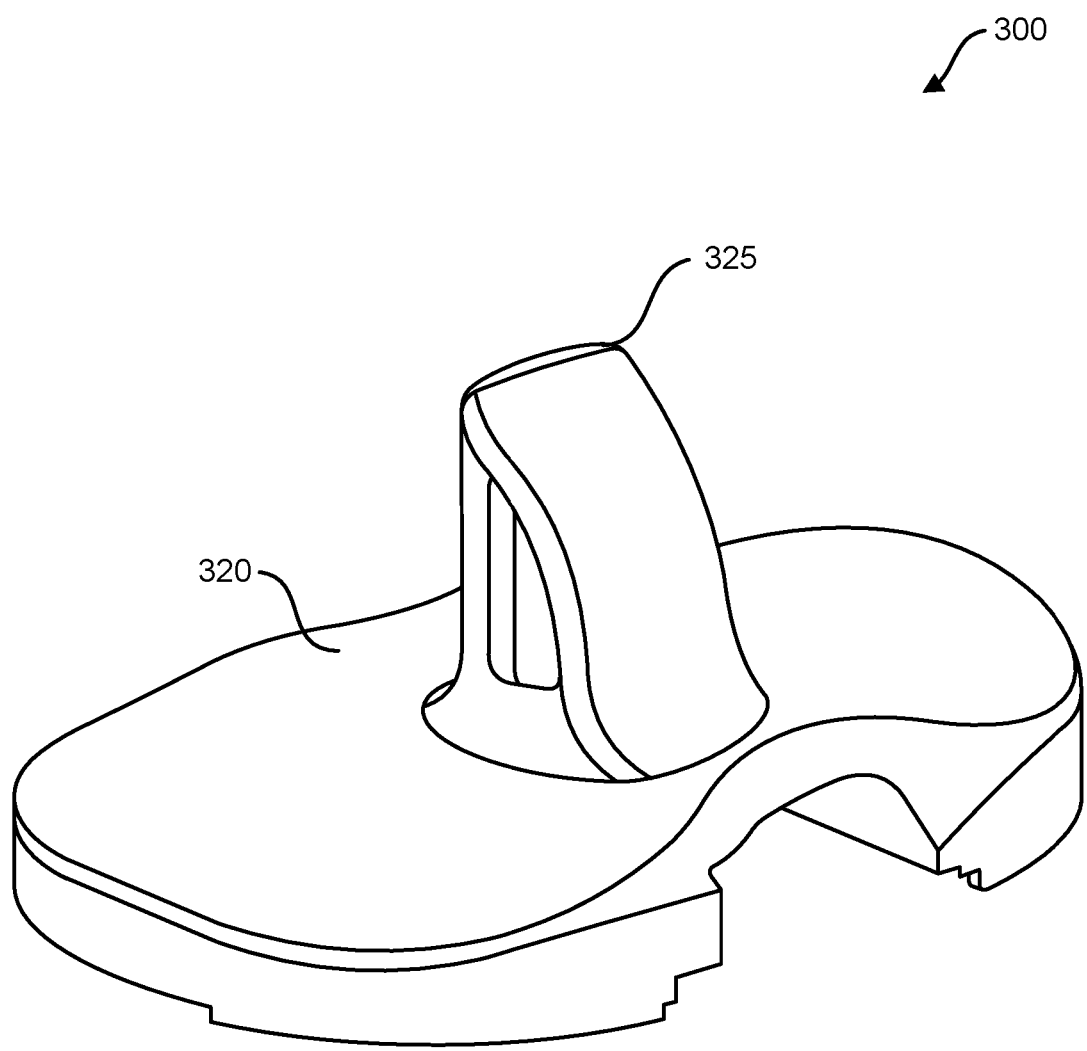
FIG. 3A is a perspective view of an example of an embodiment of an articular trial shown in FIG. 1 in accordance with one or more aspects of the present disclosure.
Figure 3B:
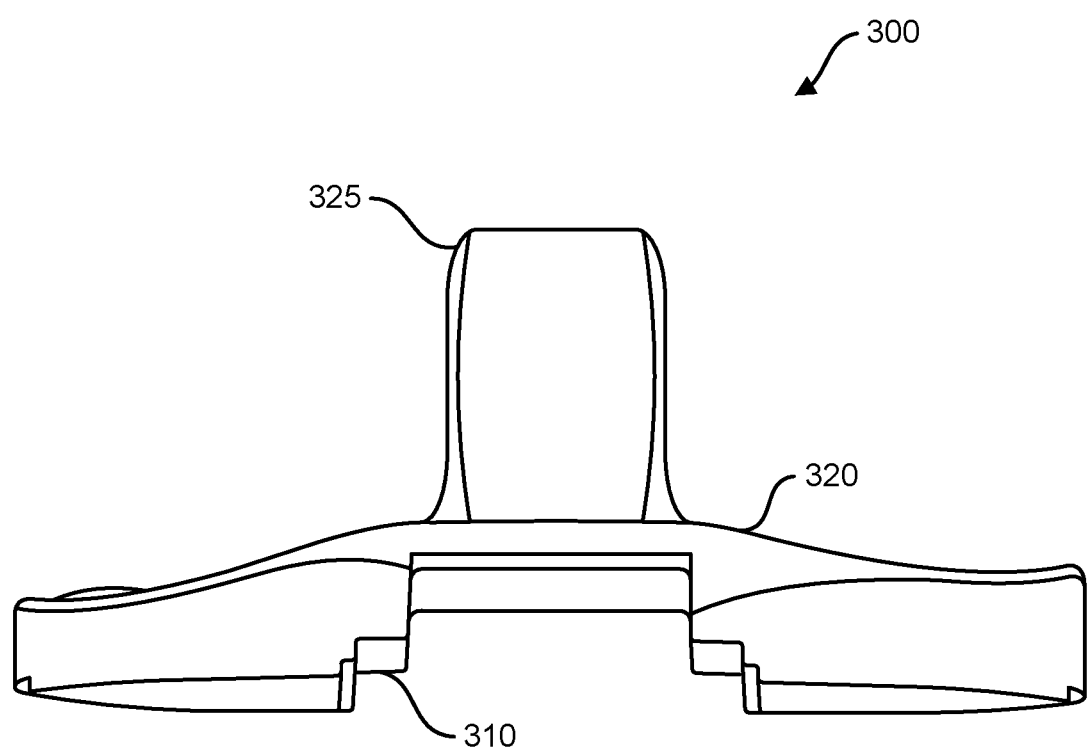
FIG. 3B is an anterior perspective view of the articular trial of FIG. 3A showing a portion of the inferior side of the articular trial.
Figure 3C:
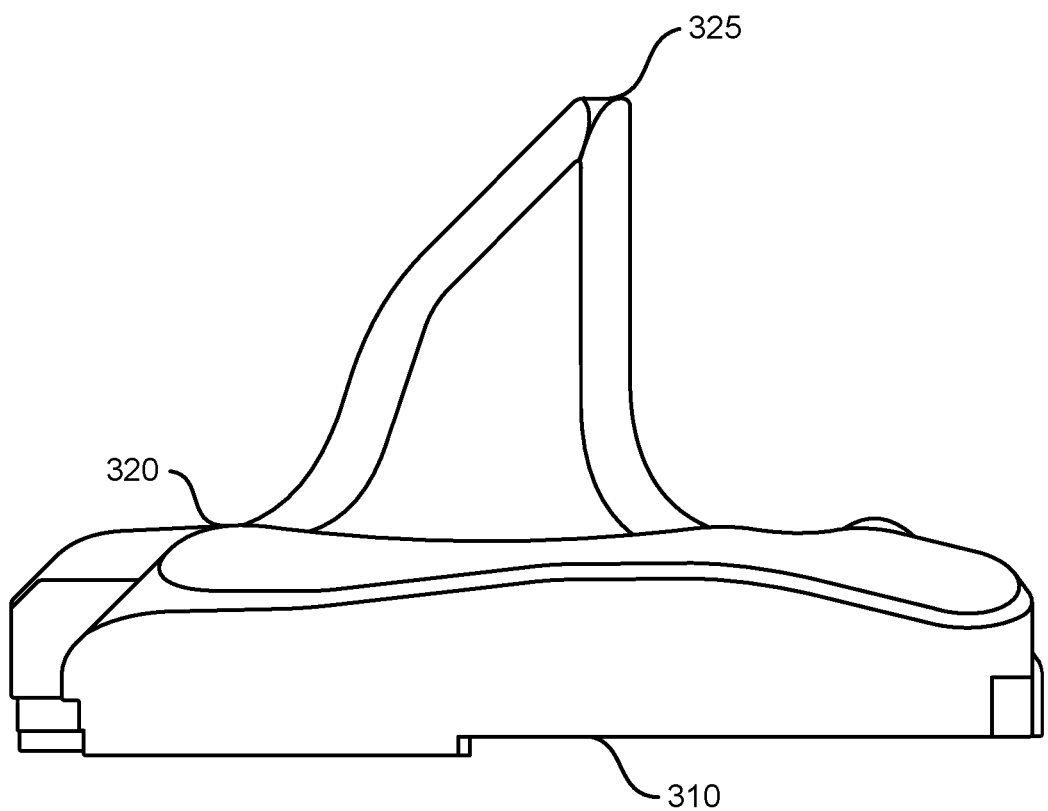
FIG. 3C is a side elevation view of the articular trial of FIG. 3A.
Figure 3D:
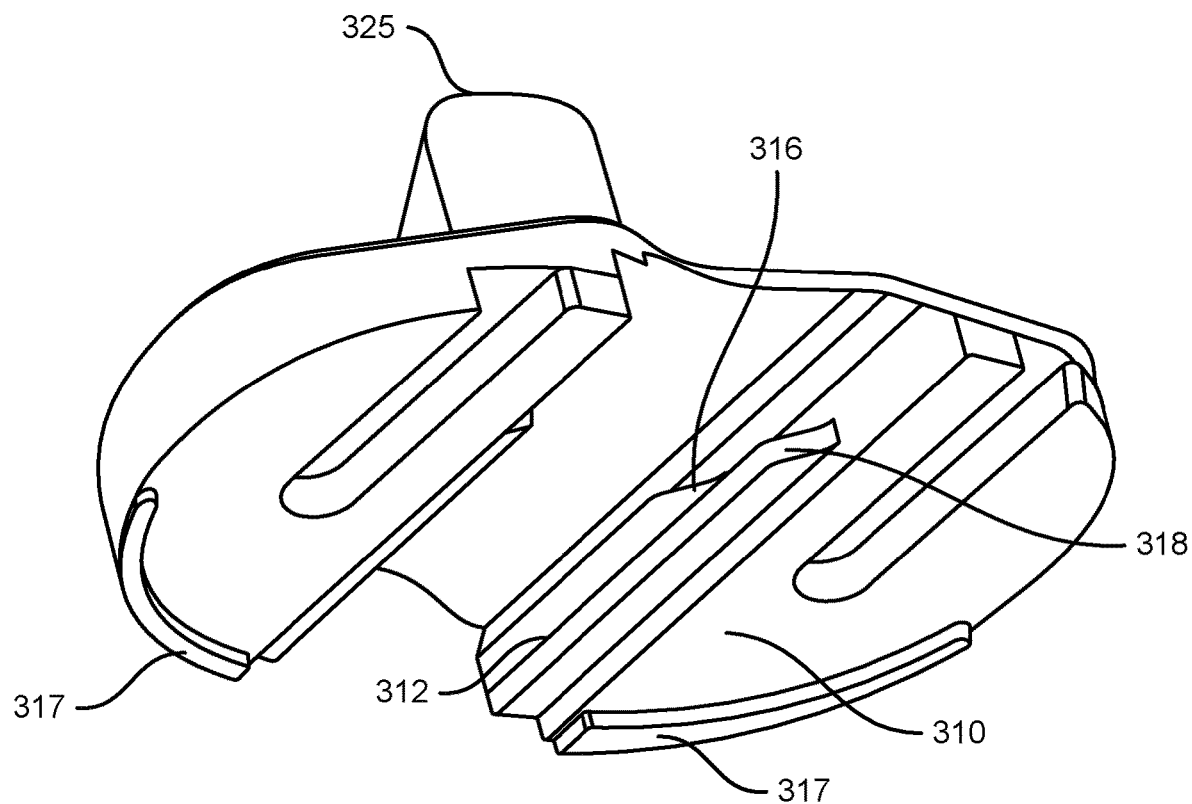
FIG. 3D is a perspective view of the articular trial of FIG. 3A showing an inferior side of the articular trial.

Referring to FIGS. 3A-3D, an example embodiment of an articular trial 300 in accordance with one or more aspects of the present disclosure is shown. As illustrated, the articular trial 300 includes an inferior side 310 with a second interlocking mechanism 312 (FIG. 3D). In use, the second interlocking mechanism 312 is arranged and configured to engage with the first interlocking mechanism 412 formed on the first spacer 400 to restrict movement of the articular trial 300 relative to the first spacer 400 when they are coupled to each other. For example, in one embodiment, the second interlocking mechanism 312 includes a second surface extending in an inferior-superior plane, the second surface arranged and configured to interact with the first surface of the first interlocking mechanism 412. The second surface depicted is oriented substantially in an anterior-posterior direction, but may be oriented medially-laterally or at some oblique orientation in other embodiments. When the second surface is engaged with the first surface, movement of the first spacer 400 relative to the articular trial 300 in a first direction is restricted. In the example shown, the first direction is along a medial-lateral axis.

As illustrated, in use, during knee trialing, the articular trial 300 is configured to be slid in a substantially anterior to posterior direction between the first spacer 400 and the femoral trial 150 or the femoral implant. In some embodiments, when the articular trial 300 is slid in a substantially anterior to posterior direction between the first spacer 400 and the femoral trial 150 or the femoral implant, the inferior side 310 of the articular trial 300 interlocks with the superior side of the first spacer 400 without significantly moving the femoral trial 150 or femoral implant superiorly relative to the first spacer 400. The term "without significantly moving" as used here refers to a limited movement, such as but not specifically limited to, substantially the height of a posterior ridge of the articular surface of the articular trial 300 relative to a central portion of the articular surface.

In one embodiment, the second interlocking mechanism 312 may include one or more second stops 316, as is illustrated in FIG. 3D, that may be oblique to the second surface. The one or more second stops 316 associated with the second interlocking mechanism 312 formed on the articular trial 300 are arranged and configured to engage with the one or more first stops 416 associated with the first interlocking mechanism 412 formed on the first spacer 400. In use, engagement of the first and second stops 416, 316 limits movement of the articular trial 300 relative to the first spacer 400 along the first surface. As shown in this embodiment, the articular trial 300 may also include an auxiliary stop 317 (FIG. 3D) arranged and configured to engage with the first spacer 400 to limit movement of the articular trial 300 relative to the first spacer 400 along the first surface. In use, the first and second stops 416, 316 may have any suitable shape arranged and configured to interact with each other to restrict movement of the articular trial 300 relative to the first spacer 400 along the first surface.

In addition, and/or alternatively, as illustrated, the second interlocking mechanism 312 may also include a second hook 318 configured to engage with the first hook 418 of the first interlocking mechanism 412 to restrict inferior and superior movement between the articular trial 300 and the first spacer 400. In use, the first and second hooks 418, 318 may have any suitable shape arranged and configured to engage, couple, attach, or the like with each other. The first hook 418 and the second hook 318 may be limited to a partial anterior-posterior length of the first spacer 400 and articular trial 300, as shown with the illustrated embodiment, or in other embodiments may extend substantially across the entire anterior-posterior length of a first spacer and articular trial. In other embodiments, a hook or functionally similar structure of either the first interlocking mechanism or the second interlocking mechanism may restrict inferior and superior movement exclusive of the other hook, for example, by hooking over an edge or outer protrusion of an opposing spacer or trial.

A feature of some embodiments, such as the illustrated embodiment, is that when the first interlocking mechanism 412 is engaged with the second interlocking mechanism 312, the combined first spacer 400 and articular trial 300 may be lifted from the tibial tray 200 (FIG. 10) and then moved anteriorly out from between the tibial tray 200 and the femoral trial 150 (FIG. 11) or the femoral implant.

The articular trial 300 of the illustrated embodiment also includes a superior side 320 (FIGS. 3A-3C) configured to interact with the femoral trial 150 or a femoral implant. The embodiment shown also includes a post 325 designed to provide posterior stabilization between the articular trial 300 and the femoral trial 150 or femoral implant. Other embodiments may not include an element such as the post 325 to provide posterior stabilization. In some embodiments, the medial and lateral portions of the articular trial may have different inferior-superior thicknesses to appropriately match or balance the anatomy of a patient.

Embodiments of the knee arthroplasty trialing system may also include a second spacer with a second thickness that is different from a thickness of a first spacer. In use, the second spacer 500 may be substantially similar in arrangement and use to the first spacer 400 described above except in thickness. That is, similar to the first spacer 400 described above, in use, the second spacer 500 is arranged and configured to couple to the tibial tray 200 and to the articular trial 300. In use, the second spacer 500 spaces the articular trial 300 from the tibial tray 200. In one embodiment, the second spacer 500 spaces the articular trial from the tibial trial 200 by a larger or smaller distance as compared to the first spacer 400. In one embodiment, the second spacer 500 is arranged and configured to couple to the tibial tray 200 and to the articular trial 300 in a lateral movement such as, but not limited to, a slidable movement along an anterior-posterior path. For the sake of brevity, elements of the second spacer 500 may not be reiterated here.

Figure 12:
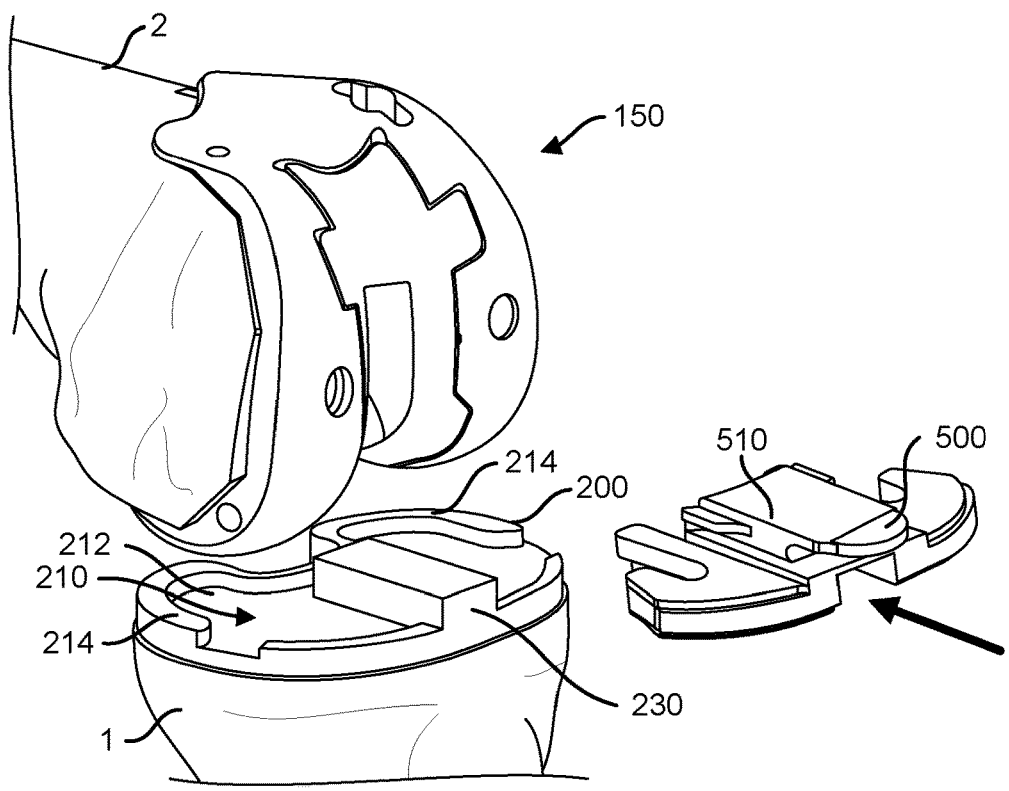
FIG. 12 is perspective view with an action arrow showing substantially anterior to posterior insertion of the spacer of FIG. 5A toward the tibial tray trial in accordance with one or more aspects of the present disclosure.
Figure 13:
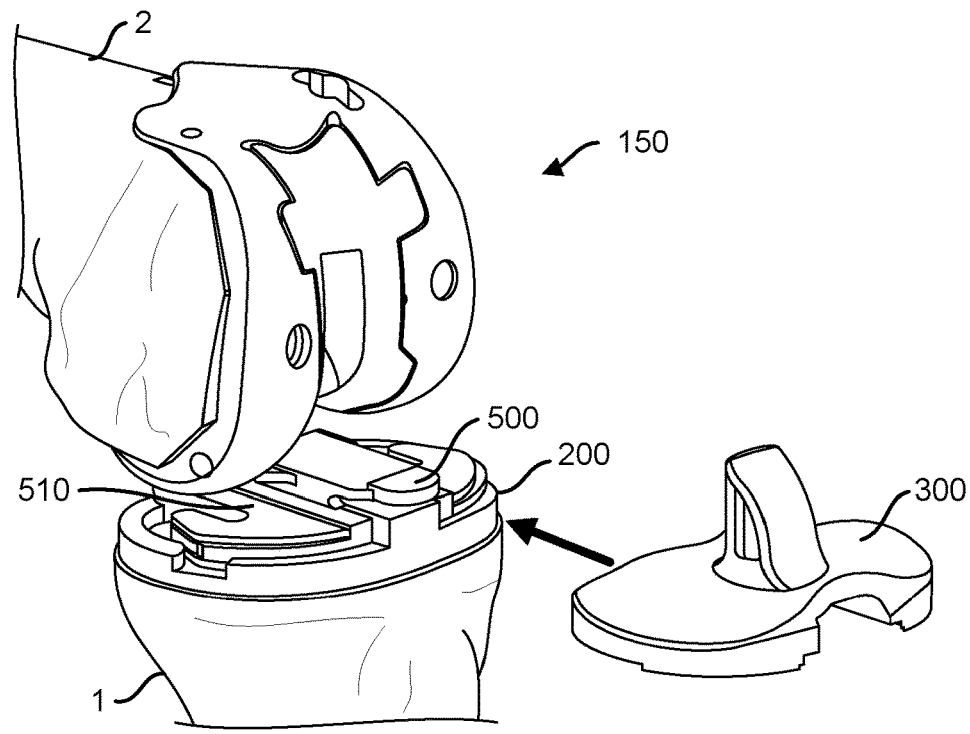
FIG. 13 is a perspective view with an action arrow showing substantially anterior to posterior insertion of the articular trial of FIG. 3A toward the spacer of FIG. 5A and the femoral trial in accordance with one or more aspects of the present disclosure.
Figure 14:
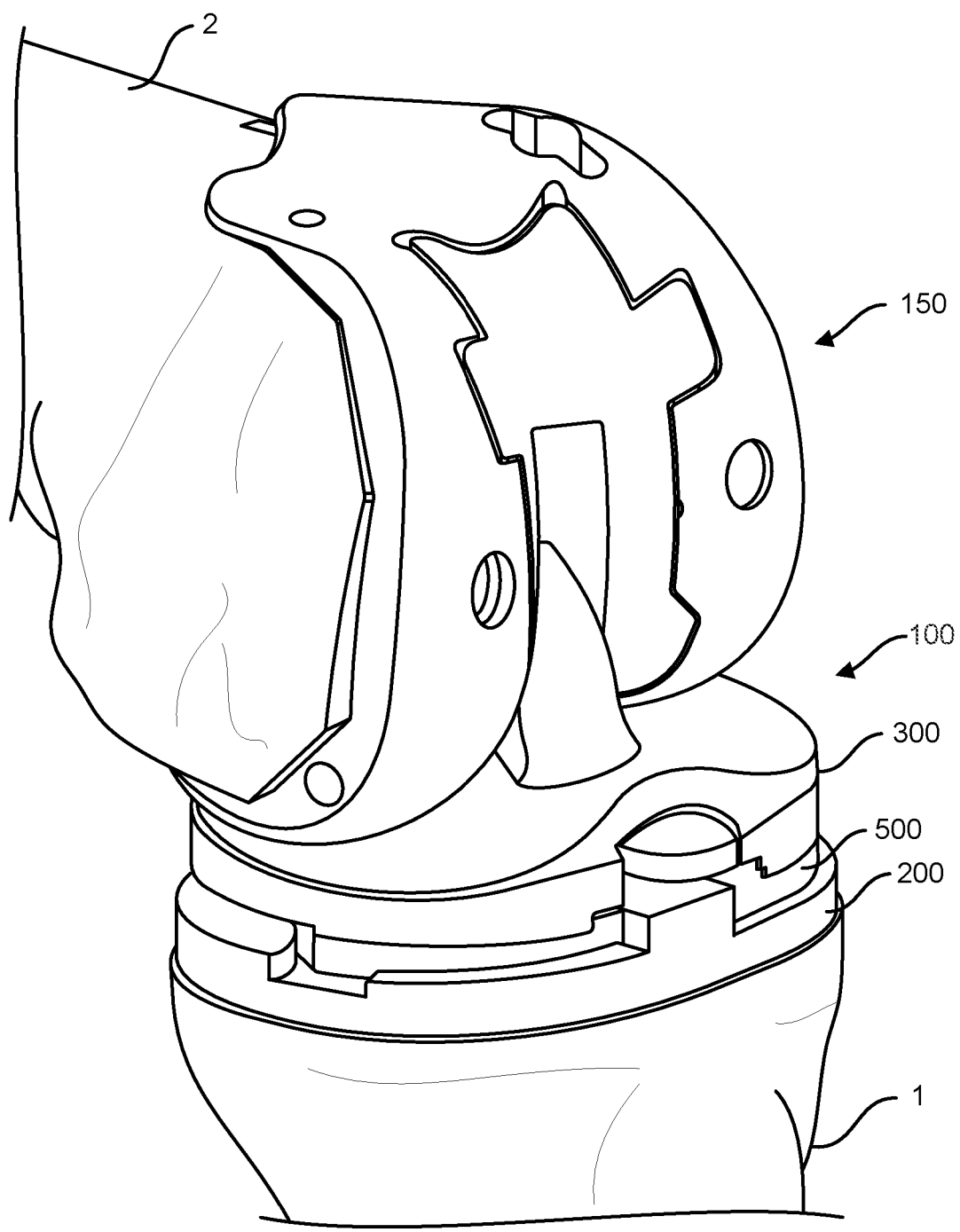
FIG. 14 is a perspective view of femoral and tibial trials for a total knee arthroplasty in place on a femur and a tibia, where the tibial trial spacer is thicker than the tibial trial spacer of FIG. 1.

In one example embodiment, the second spacer 500 may be, in its operative part, thicker than the first spacer 400. As shown in FIGS. 5A-5D, the second spacer 500 has a superior side 510 with a first interlocking mechanism 512 and an inferior side 520. The illustrated inferior side 520 is arranged and configured to be selectively connectable, attached, coupled, or the like with at least a portion of the tibial tray 200 to restrict motion of the second spacer 500 relative to the tibial tray 200 when the second spacer 500 is connected to the tibial tray 200, as shown in FIGS. 13 and 14. Specifically, in the illustrated embodiment, the inferior side 520 of the second spacer 500 may include a periphery 522 (FIGS. 5B and 5C) sized and configured to fit within the indention 212 formed in the superior surface 210 of the tibial tray 200, as shown in FIGS. 12-14. Thus arranged, the periphery 522 formed on the second spacer 500 and the indentation 212 formed in the superior surface 210 of the tibial tray 200 restrict anterior, posterior, medial, and lateral movement of the second spacer 500 relative to the tibial tray 200.

Figure 5A:
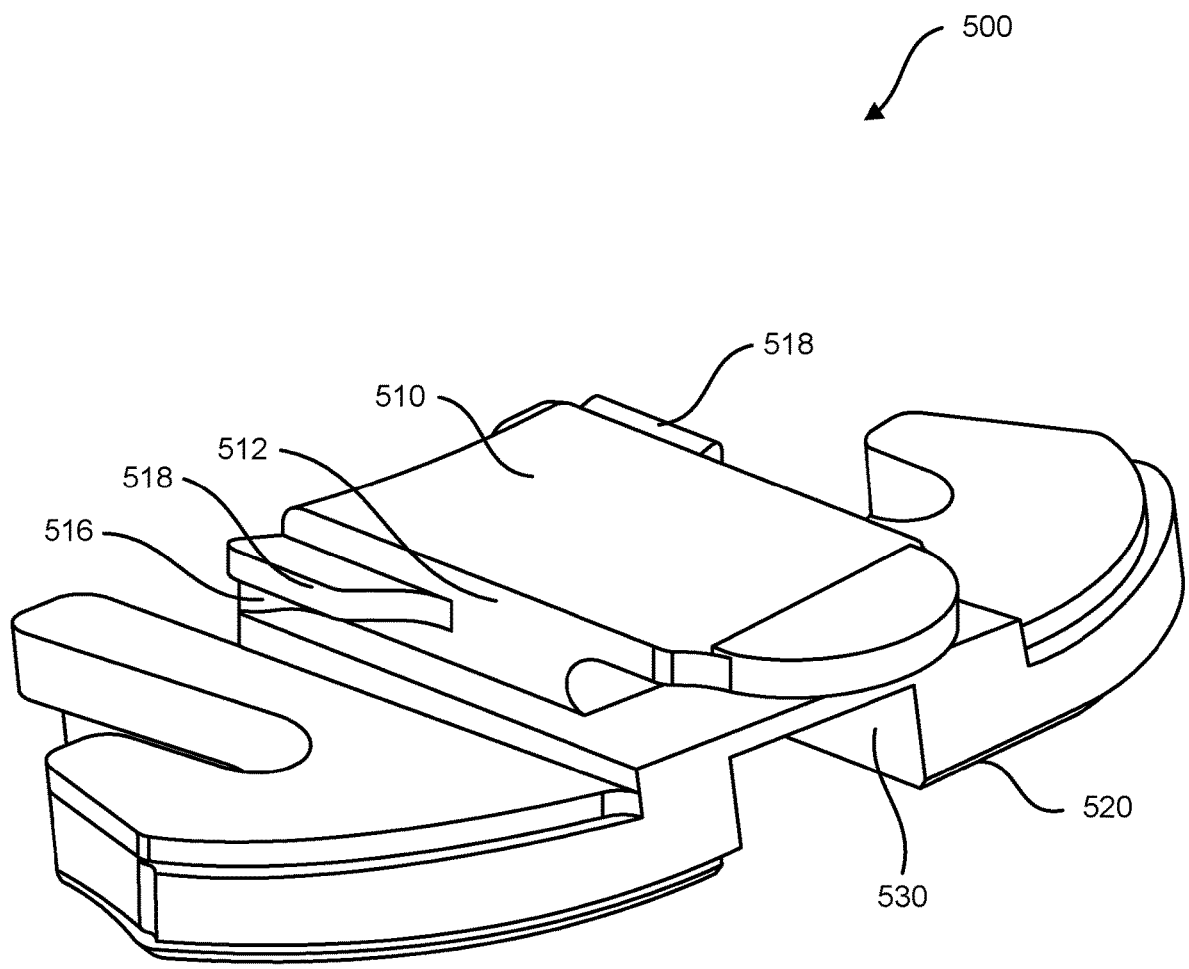
FIG. 5A is perspective view of an alternate example of an embodiment of a spacer that may be used with the total knee arthroplasty of FIG. 1 in accordance with one or more aspects of the present disclosure, the spacer having a greater thickness than the spacer of FIG. 4A.
Figure 5B:
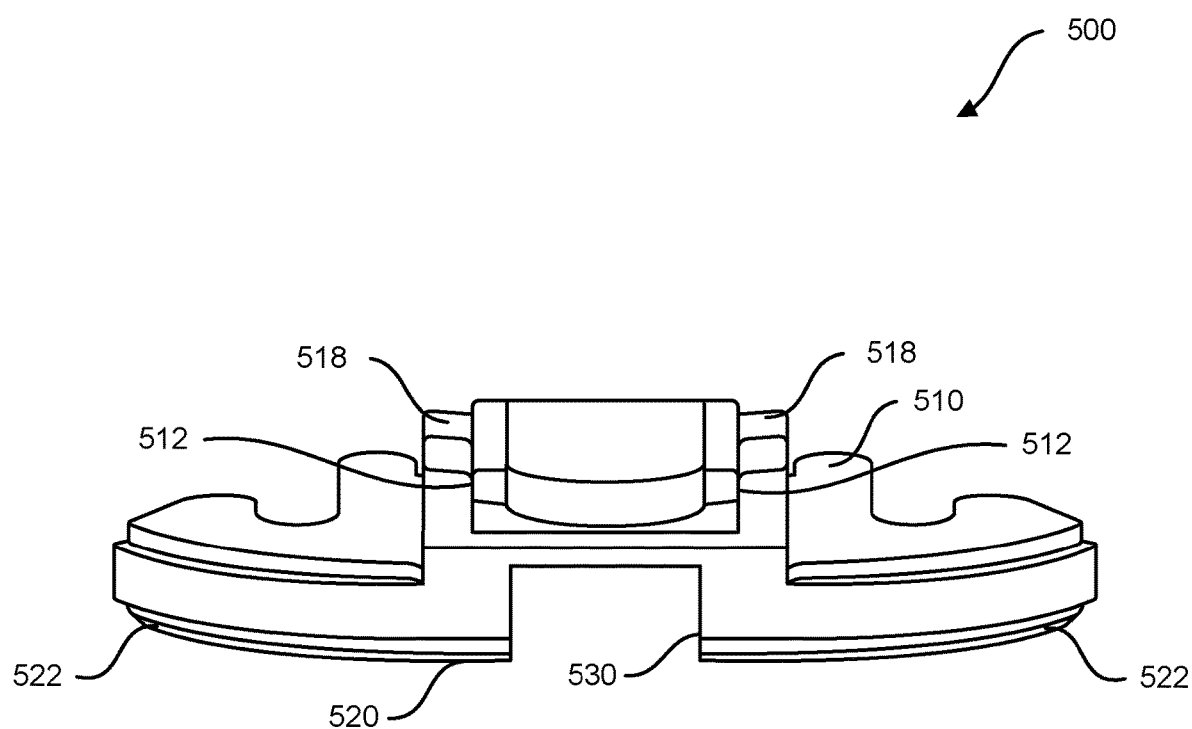
FIG. 5B is an anterior perspective view of the spacer of FIG. 5A showing a portion of the superior side of the spacer.
Figure 5C:
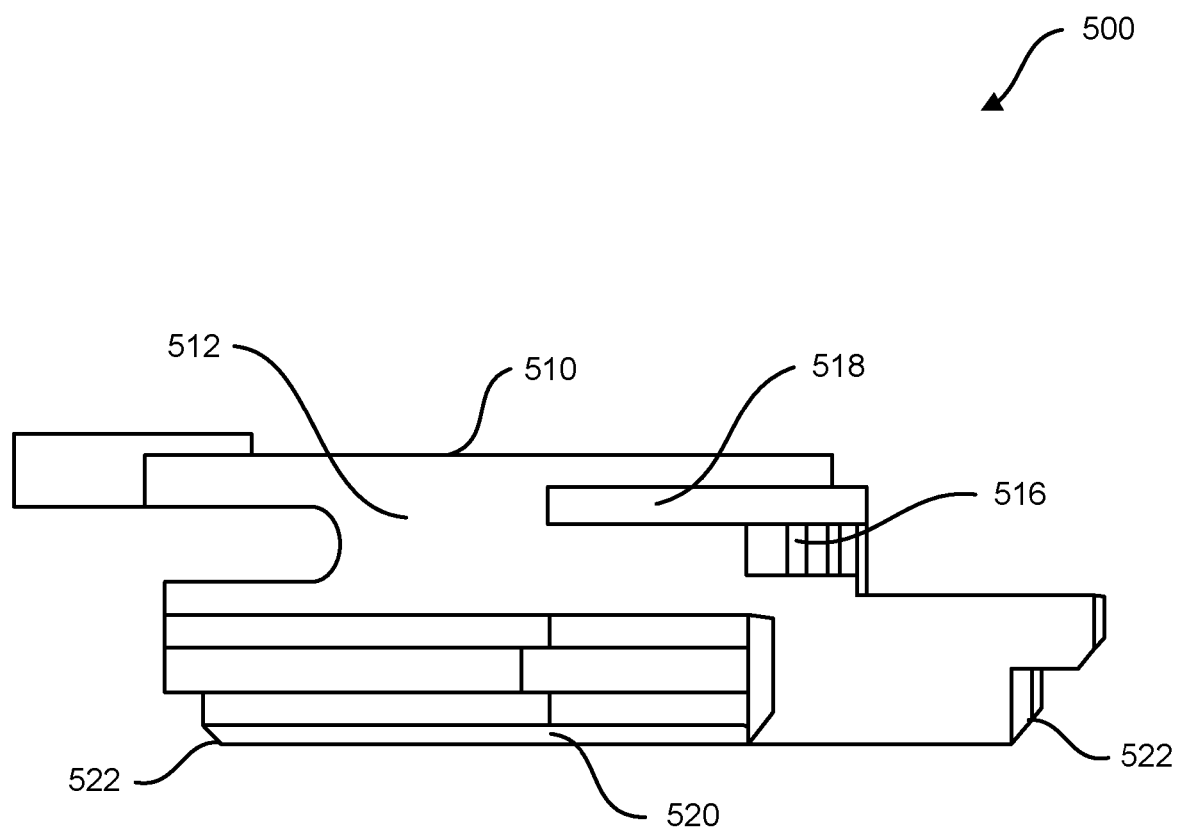
FIG. 5C is a side elevation view of the spacer of FIG. 5A.
Figure 5D:
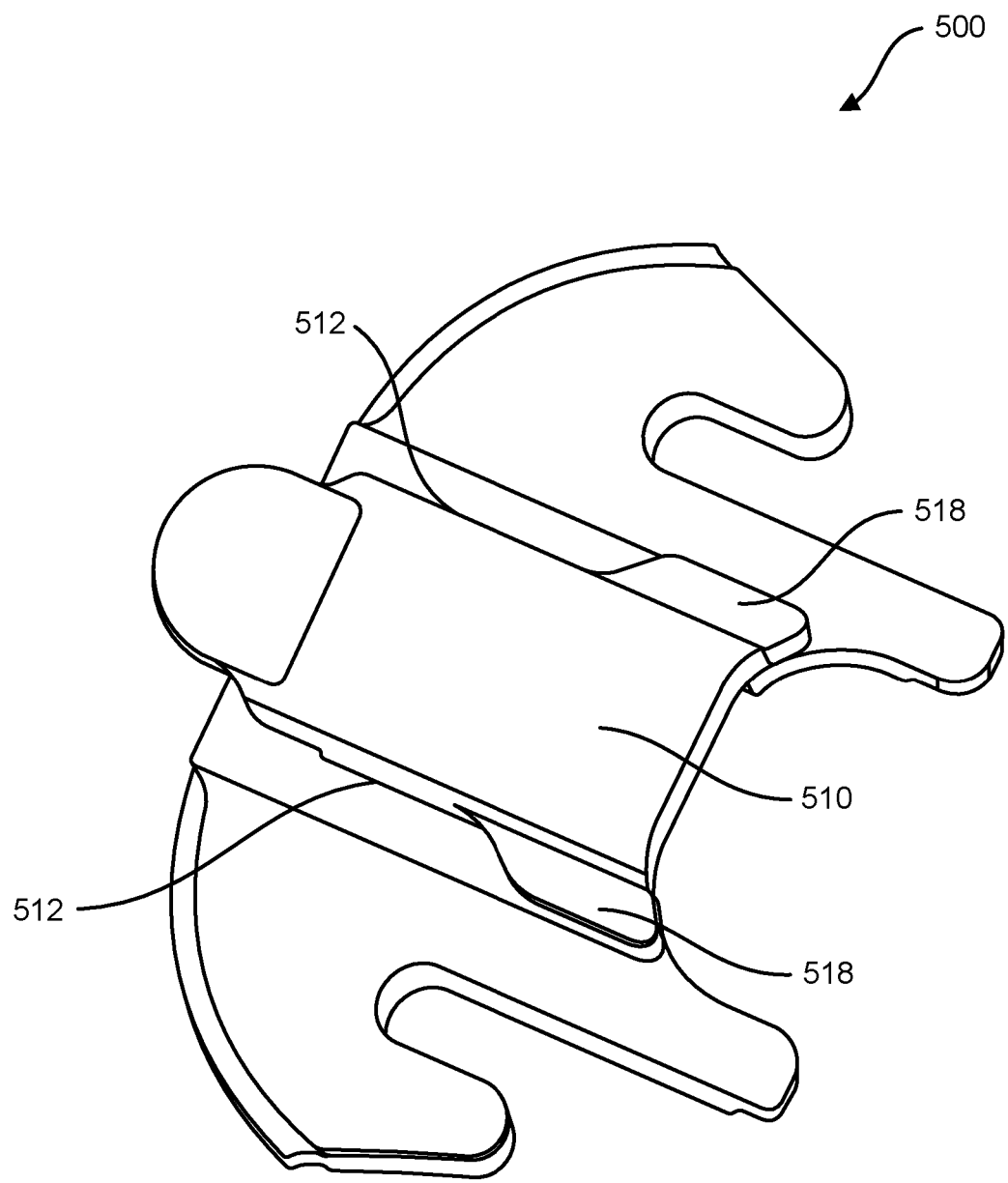
FIG. 5D is a perspective view of the spacer of FIG. 5A showing a superior side of the spacer.

Referring to FIGS. 5A and 5B, the second spacer 500 may also include a notch 530 on the inferior side 520 of the spacer 500. In use, the notch 530 is sized and shaped to receive the ridge 230 extending from the superior surface 210 of the tibial tray 200 as previously described (FIGS. 12-14). Thus arranged, the interaction between the notch 530 formed in the second spacer 500 and the ridge 230 formed on the tibial tray 200 restricts medial and lateral movement of the second spacer 500 relative to the tibial tray 200. In other embodiments without a ridge type structure, coupling between elements such as the indention 212 and the ridge 214 of the tibial tray 200 and the periphery 522 of the second spacer 500 may adequately restrict medial and lateral movement of the second spacer 500 relative to the tibial tray 200.

Similar to the first spacer 400, the second spacer 500 may include a first interlocking mechanism 512. In the illustrated embodiment, the first interlocking mechanism 512 includes at least a first surface in an inferior-superior plane. The first surface shown is oriented substantially in an anterior-posterior direction, but in other embodiments could be medially-laterally oriented or at some oblique orientation. The first interlocking mechanism shown also includes a first stop 516 oblique to the first surface, as shown best in FIGS. 5A and 5C. The first interlocking mechanism 512 may also include a pair of first hooks, projections, laterally-extending ridges, or the like 518 configured to engage with the articular trial 300 and restrict inferior and superior movement between the articular trial and the spacer.

In use, similar to the first spacer, the second interlocking mechanism 312 of the articular trial 300 is configured to engage with the first interlocking mechanism 512 of the second spacer 500. In one embodiment, the first interlocking mechanism 512 (e.g., the first surface of the first interlocking mechanism 512) may be oriented substantially in an anterior posterior direction, but may be oriented medially-laterally or at some oblique orientation in other embodiments. When the second interlocking mechanism 312 is engaged with the first interlocking mechanism 512 (e.g., the first surface of the first interlocking mechanism 512), movement of the second spacer 500 relative to the articular trial 300 in a first direction is restricted. In the example shown, the first direction is along a medial-lateral axis.

As previously described, in use, the illustrated articular trial 300 is configured to be slid in a substantially anterior to posterior direction between the second spacer 500 and the femoral trial 150 or the femoral implant. In some embodiments, when the articular trial 300 is slid in a substantially anterior to posterior direction between the second spacer 500 and the femoral trial 150 or the femoral implant, the inferior side 310 of the articular trial 300 interlocks with the superior side of the second spacer 500 without significantly moving the femoral trial 150 or femoral implant superiorly relative to the second spacer 500.

In one embodiment, as previously described, the second interlocking mechanism 312 may include one or more second stops 316, as is illustrated in FIG. 3D, that may be oblique to the second surface of the second interlocking mechanism 312 and engageable with the one or more first stops 516 associated with the first interlocking mechanism 512 formed on the second spacer 500. In use, engagement of the first and second stops 516, 316 limits movement of the articular trial 300 relative to the second spacer 500 along the first surface. As shown in this embodiment, the articular trial 300 may also include an auxiliary stop 317 (FIG. 3D) arranged and configured to engage with the second spacer 500 to limit movement of the articular trial 300 relative to the second spacer 500 along the first surface.

In addition, and/or alternatively, as previously described, the second interlocking mechanism 312 may also include a second hook 318 configured to engage with the first hook 518 of the first interlocking mechanism 512 to restrict inferior and superior movement between the articular trial 300 and the second spacer 500. The first hook 518 and the second hook 318 may be limited to a partial anterior-posterior length of the second spacer 500 and articular trial 300, as shown with the illustrated embodiment, or in other embodiments may extend substantially across the entire anterior-posterior length of a second spacer and articular trial. In other embodiments, a hook or functionally similar structure of either the first interlocking mechanism or the second interlocking mechanism may restrict inferior and superior movement exclusive of the other hook, for example, by hooking over an edge or outer protrusion of an opposing spacer or trial.

A feature of some embodiments, such as the illustrated embodiment, is that when the first interlocking mechanism 512 is engaged with the second interlocking mechanism 312, the combined second spacer 500 and articular trial 300 may be lifted from the tibial tray 200 and then moved anteriorly out from between the tibial tray 200 and the femoral trial 150 or the femoral implant.

In other embodiments, a second spacer may be thinner than the first spacer in its operative part. Some embodiments may include more than two spacers, each with operative parts of different thicknesses.

Referring to FIGS. 6-14, an example method embodiment in accordance with one or more aspects of the present disclosure will now be shown and described. The illustrated embodiment is a method of determining an appropriate size for a knee arthroplasty device by using trials. The depicted method includes placing a tibial tray 200 on a patient's tibia 1. In some embodiments, the tibial tray 200 is a trial not configured and composed for permanent implantation. In other embodiments, the method may use a final, implantable tibial tray in the disclosed acts of the method. The disclosed method also includes placing a femoral component, such as the femoral trial 150, on the patient's femur 2. In some embodiments, the femoral component is a trial not configured and composed for permanent implantation. In other embodiments, the method may use a final, implantable femoral component in the disclosed acts of the method.

Figure 6:
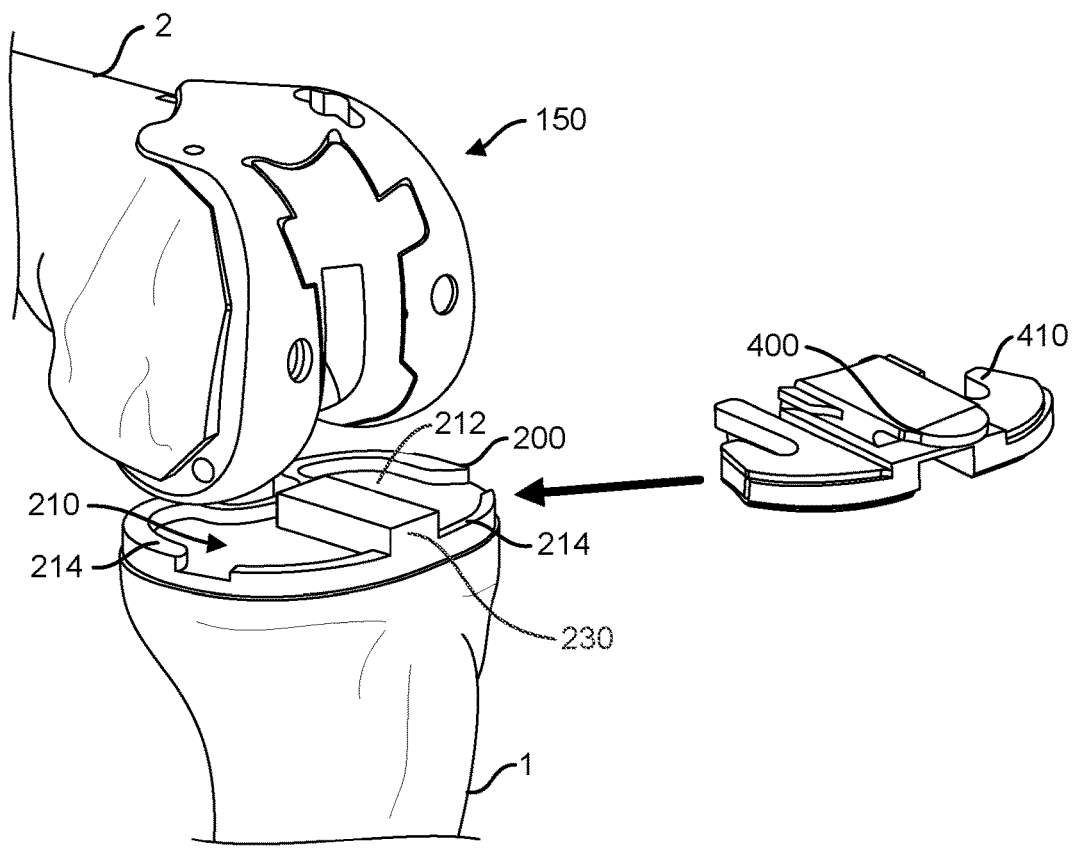
FIG. 6 is a perspective view with an action arrow showing substantially anterior to posterior insertion of the spacer of FIG. 4A toward the tibial tray trial in accordance with one or more aspects of the present disclosure.
Figure 7:
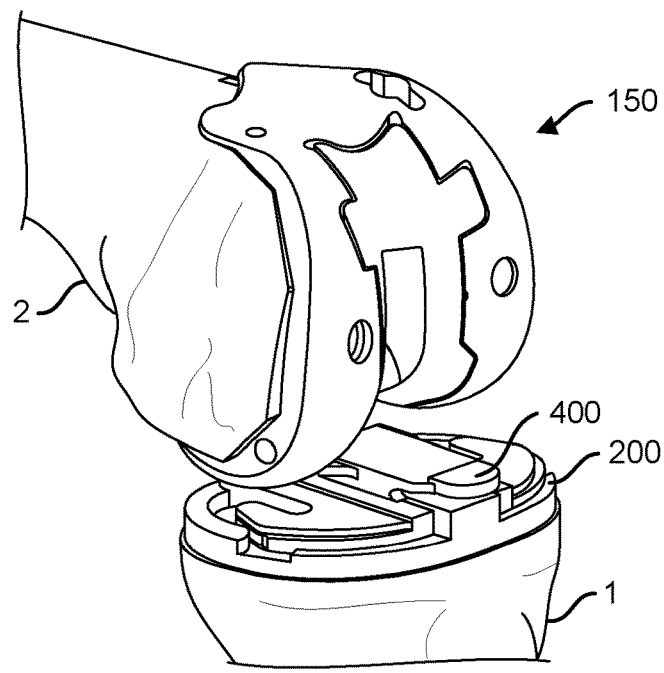
FIG. 7 is a perspective view of the spacer of FIG. 4A in place on the tibial tray trial.

As shown in FIGS. 6 and 7, method embodiments include connecting a first spacer 400 with a first thickness to the tibial tray 200. As shown in FIG. 6, the act of connecting the first spacer 400 to the tibial tray 200 may include moving the first spacer 400 in a substantially anterior to posterior direction and in a substantially superior to inferior direction. The action arrow drawn in FIG. 6 shows a combined anterior to posterior and superior to inferior vector direction, but in other embodiments anterior to posterior and superior to inferior movements may be done in succession or in multiple successions. In other embodiments, movement of a first spacer for connection to a tibial tray may be in a medial-lateral direction or in an effective oblique direction, as is compatible with the spacer and tibial tray being employed. FIG. 7 depicts the first spacer 400 after its connection to the tibial tray 200.

Figure 8:
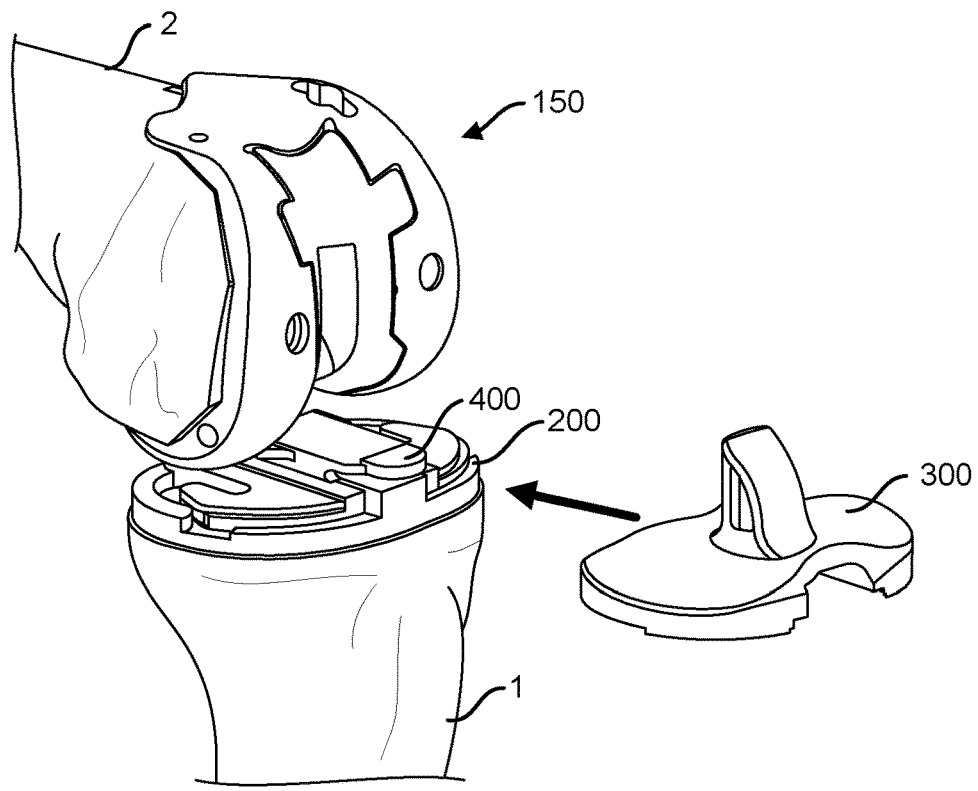
FIG. 8 is a perspective view with an action arrow showing substantially anterior to posterior insertion of the articular trial of FIG. 3A toward the spacer of FIG. 4A and the femoral trial in accordance with one or more aspects of the present disclosure.
Figure 9:
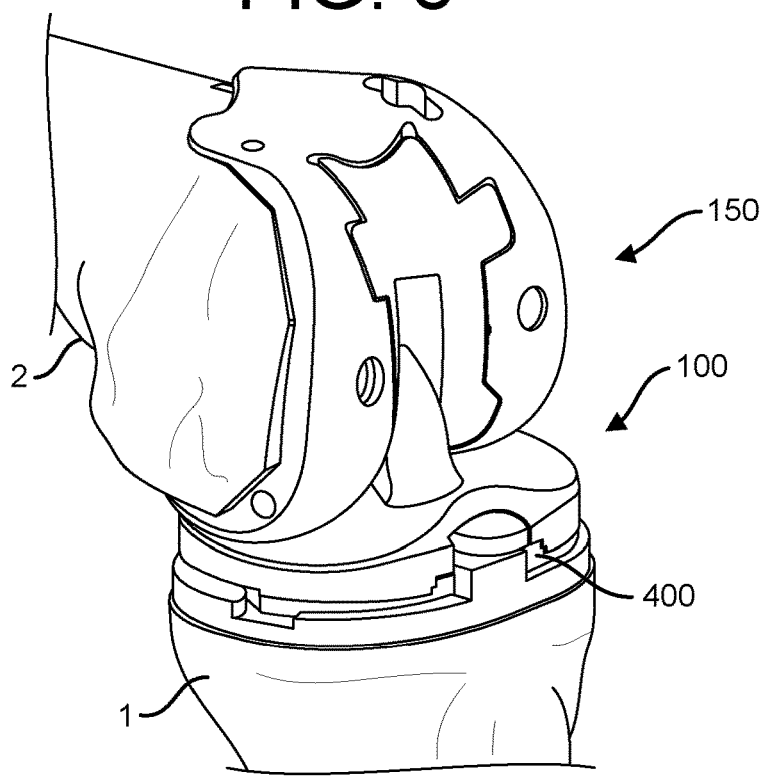
FIG. 9 is a perspective view of the articular trial in place between the spacer and the femoral trial.
Figure 10:
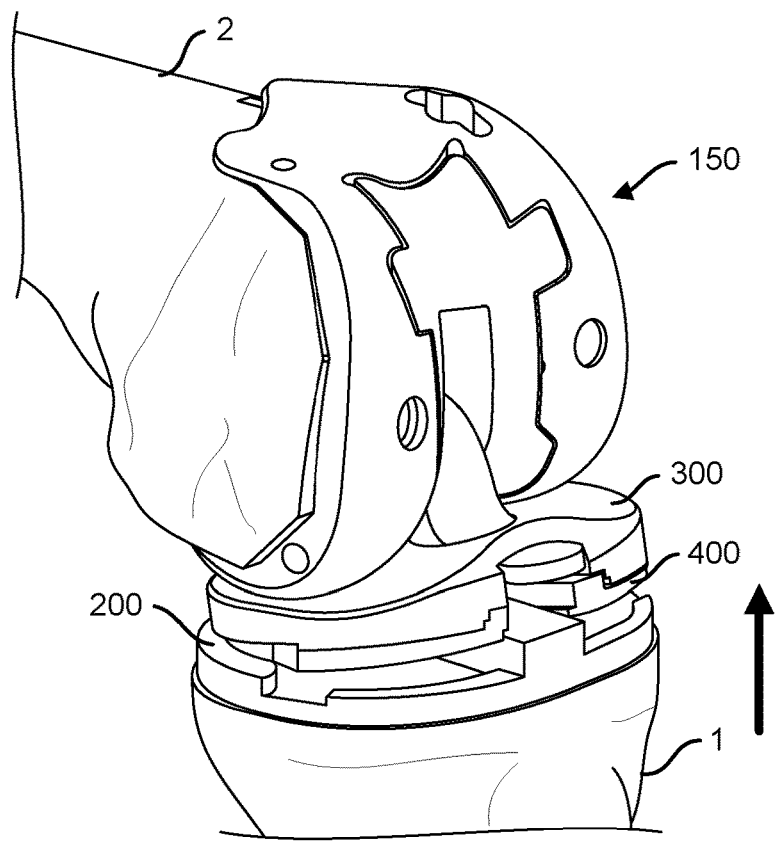
FIG. 10 is a perspective view with an action arrow showing superior lifting of the articular trial and spacer relative to the tibial tray trial in accordance with one or more aspects of the present disclosure.
Figure 11:
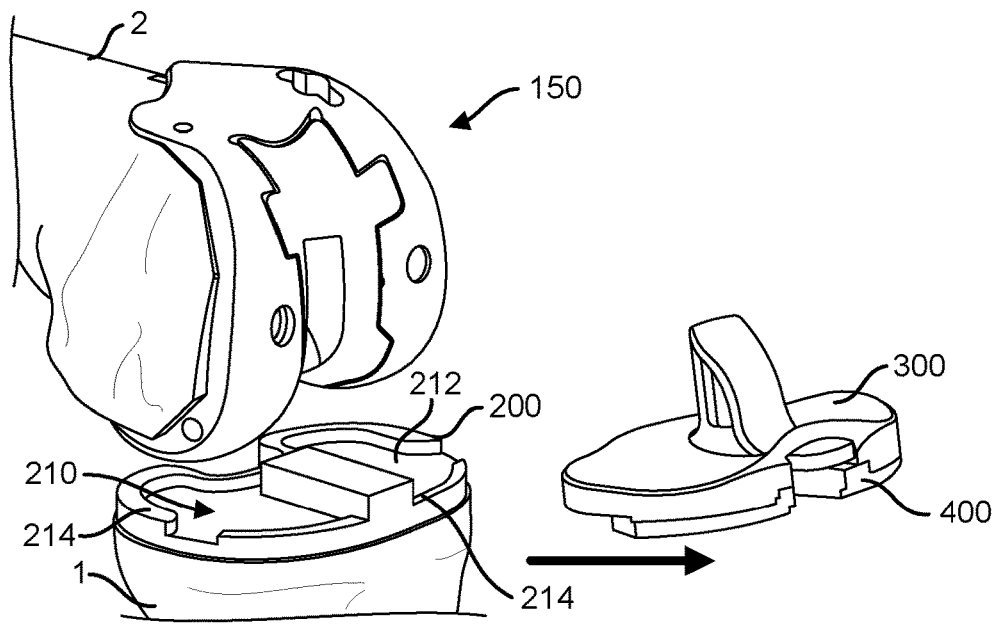
FIG. 11 is a perspective view with an action arrow showing substantially posterior to anterior removal of the articular trial and spacer from the joint space in accordance with one or more aspects of the present disclosure.

As illustrated in FIGS. 8 and 9, the method may include inserting an articular trial 300 on a superior side 410 of the first spacer 400 between the first spacer 400 and the femoral component 150. The act of inserting the articular trial 300 on the superior side 410 of the first spacer 400 between the first spacer 400 and the femoral component 150 specifically illustrated includes sliding the articular trial 300 substantially anteriorly to posteriorly relative to the first spacer 400, as indicated by the action arrow in FIG. 8. In this embodiment, the articular trial 300 is inserted on a superior side 410 of the first spacer 400 between the first spacer 400 and the femoral component 150 without significantly moving the femoral component 150 superiorly relative to the first spacer 400. As shown, this sliding insertion of the articular trial 300 includes interlocking an inferior side 310 of the articular trial 300 with the superior side 410 of the first spacer 400. An interlocked articular trial 300 and first spacer 400 are shown in FIG. 9. When interlocked in this manner, medial and lateral movement between the articular trial 300 and the first spacer 400 are restricted at least by the first interlocking mechanism 412 with its first surface in an inferior-superior plane and the second interlocking mechanism 312 with its second surface in an inferior-superior plane, as described in more detail above. Also when interlocked in this manner, inferior and superior movement between the articular trial 300 and the first spacer 400 are restricted at least by the first hook 418 of the first interlocking mechanism 412 and the second hook 318 of the second interlocking mechanism 312, as described in more detail above. Additionally when interlocked in this manner, anterior movement between the articular trial 300 and the first spacer 400 is restricted at a predefined limit at least by the one or more second stops 316 of the second interlocking mechanism 312 that are oblique to the second surface of the second interlocking mechanism 312 when engaged with one or more of the first stops 416, as described in more detail above.

After the components are assembled, as shown in FIG. 9, with the first spacer 400 and articular trial 300 connected and inserted, embodiments of the method include assessing joint balance. Assessment of joint balance may be accomplished in any effective known or later developed manner. Assessment may include flexing and extending the joint, twisting the joint about a longitudinal axis of the tibia, and moving the patient's foot medially and laterally. If the assessment is satisfactory, the first spacer 400 and the articular trial 300 may be removed from the joint and final, and implantable components may be placed. The act of removing the first spacer 400 and the articular trial 300 may include lifting at least part of the first spacer 400 and the articular trial 300 together in a substantially inferior to superior direction, as indicated by the action arrow in FIG. 10. Lifting at least a part of the devices may include a pivoting action such as moving an anterior portion of the devices more superiorly sooner than a posterior portion of the devices. Some embodiments, however, may include only a uniform inferior to superior movement.

If the assessment is not satisfactory, acts of the method may include removing the first spacer 400 and the articular trial 300 (FIGS. 10 and 11) and connecting a second spacer with a second thickness, such as second spacer 500, to the tibial tray 200 (FIGS. 12 and 13). In one embodiment, the second spacer 500 has a second thickness that is in operative part thicker than the first spacer 400. As used herein throughout, the term "in operative part" means a part that affects the overall spacing between tibial tray 200 and the articular trial 300 when the components are assembled. In the illustrated example, as a result of the operatively thicker part of the second spacer 500 (FIG. 14) compared to the operative part of the first spacer 400 (FIG. 9), the space between the tibial tray 200 and the articular trial 300 is observably greater in FIG. 14 than in FIG. 9. In other embodiments where the assessment led to a conclusion that the first spacer 400 was too large, a second spacer with a second thickness may be used that is in operative part thinner than the first spacer 400.

As illustrated in FIGS. 13 and 14, the method may include inserting an articular trial 300 on a superior side 510 of the second spacer 500 between the second spacer 500 and the femoral component 150 without significantly moving the femoral component superiorly relative to the second spacer 500. The act of inserting the articular trial 300 on the superior side 510 of the second spacer 500 between the second spacer 500 and the femoral component 150 specifically illustrated includes sliding the articular trial 300 substantially anteriorly to posteriorly relative to the second spacer 500, as indicated by the action arrow in FIG. 13. As shown, this sliding insertion includes interlocking an inferior side 310 of the articular trial 300 with the superior side 510 of the second spacer 500. An interlocked articular trial 300 and second spacer 500 are shown in FIG. 14. When interlocked in this manner, medial and lateral movement between the articular trial 300 and the second spacer 500 are restricted at least by the first interlocking mechanism 512 with its first surface in an inferior-superior plane and the second interlocking mechanism 312 with its second surface in an inferior-superior plane, as described in more detail above. Also when interlocked in this manner, inferior and superior movement between the articular trial 300 and the second spacer 500 are restricted at least by the first hook 518 of the first interlocking mechanism 512 and the second hook 318 of the second interlocking mechanism 312, as described in more detail above. Additionally when interlocked in this manner, anterior movement between the articular trial 300 and the second spacer 500 is restricted at a predefined limit at least by the one or more second stops 316 of the second interlocking mechanism 312 that are oblique to the second surface of the second interlocking mechanism 312 when engaged with one or more of the first stops 516, as described in more detail above.

After the components are assembled as shown in FIG. 14 with the second spacer 500 and articular trial 300 connected and inserted, embodiments of the method include assessing joint balance. Assessment of joint balance may be accomplished in any effective known or later developed manner. Assessment may include flexing and extending the joint, twisting the joint about a longitudinal axis of the tibia, and moving the patient's foot medially and laterally. If the assessment is satisfactory, the second spacer 500 and the articular trial 300 may be removed from the joint and final, and implantable components may be placed. The act of removing the second spacer 500 and the articular trial 300 may include lifting at least part of the second spacer 500 and the articular trial 300 together in a substantially inferior to superior direction. Lifting at least a part of the devices may include a pivoting action such as moving an anterior portion of the devices more superiorly sooner than a posterior portion of the devices. Some embodiments, however, may include only a uniform inferior to superior movement.

If the assessment is not satisfactory, acts of the method may include removing the second spacer 500 and the articular trial 300 and connecting a different spacer with another thickness to the tibial tray 200. This type of spacer placement and assessment may be continued until a satisfactorily sized and shaped spacer and articular trial are found.

Various embodiments of the system in whole or its components individually may be made from any biocompatible material. For example and without limitation, biocompatible materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

Terms such as superior, inferior, anterior, posterior, longitudinal, proximal, distal, medial, lateral, width, height, length, against, over, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof.

The foregoing description has broad application. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited.

The phrases "at least one", "one or more", and "and/or", as used herein, are open-ended expressions that are both conjunctive and disjunctive in operation. The terms "a" (or "an"), "one or more" and "at least one" can be used interchangeably herein. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. Moreover, the following claims are hereby incorporated into this Detailed Description by this reference, with each claim standing on its own as a separate embodiment of the present disclosure.

What is claimed:

1. A tibial trial comprising:
a tibial tray;
a spacer with a superior side and an inferior side, wherein the inferior side is sized and shaped to connect with at least a portion of the tibial tray to restrict motion of the spacer relative to the tibial tray when connected to the tibial tray, the spacer comprising a first interlocking mechanism extending superiorly therefrom, the first interlocking mechanism including medial and lateral sidewalls and a plurality of rails extending laterally from the medial and lateral sidewalls of the first interlocking mechanism, the plurality of rails extending in an anterior to posterior direction, the plurality of rails defining a groove along the medial and lateral sidewalls of the first interlocking mechanism;
an articular trial with an inferior side and with a superior side configured to interact with a femoral trial or a femoral implant, the articular trial being configured to be slid in an anterior to posterior direction between the spacer and the femoral trial or the femoral implant, the articular trial comprising a recess formed in the inferior surface thereof, the recess arranged and configured to receive the first interlocking mechanism, the articular trial further including a plurality of guide rails extending laterally into the recess, the plurality of guide rails extending in an anterior to posterior direction; and
wherein when the articular trial is slid in an anterior to posterior direction between the spacer and the femoral trial or the femoral implant, the plurality of guide rails on the articular trial interlock with the grooves defined by the plurality of rails extending from the medial and lateral sidewalls of the first interlocking mechanism of the spacer without moving the femoral trial or femoral implant superiorly relative to the spacer.

2. The tibial trial of claim 1, wherein the tibial tray includes at least a partial indentation sized and shaped to receive a portion of the spacer.

3. The tibial trial of claim 2, wherein the at least a partial indentation is formed by a rim about a portion of a perimeter of the tibial tray.

4. The tibial trial of claim 3, wherein a portion of the inferior side of the spacer fits within the rim on the tibial tray when the inferior side of the spacer is connected to the tibial tray.

5. The tibial trial of claim 1, wherein the tibial tray includes a ridge across a superior portion of the tibial tray.

6. The tibial trial of claim 5, wherein a length of the ridge is in an anterior-posterior direction.

7. The tibial trial of claim 5, wherein the ridge is centrally located on the tibial tray.

8. The tibial trial of claim 5, wherein the spacer includes a notch on its inferior side to receive the ridge of the tibial tray.

9. The tibial trial of claim 1, wherein when the articular trial is slid in an anterior to posterior direction relative to the spacer, the inferior side of the articular trial interlocks with the superior side of the spacer such that anterior movement between the articular trial and the spacer is stopped at a predefined limit.

10. The tibial trial of claim 1, wherein after the articular trial has been slid between the spacer and the femoral trial or the femoral implant to a point where the inferior side of the spacer is connected to the tibial tray and the inferior side of the articular trial is interlocked with the articular trial, the combined spacer and articular trial is first lifted from the tibial tray by the articular trial and then moved anteriorly out from between the tibial tray and the femoral trial or the femoral implant.

11. The tibial trial of claim 1, wherein:
the plurality of rails of the spacer include a first stop oblique to the groove, and the guide rail of the articular trial includes a second stop oblique to the guide rail that is engageable with the first stop to limit movement of the articular trial relative to the spacer along the groove.

12. The tibial trial of claim 11, wherein the plurality of rails of the spacer includes a first hook to engage with the guide rail of the articular trial to restrict inferior and superior movement between the articular trial and the spacer.

13. The tibial trial of claim 11, wherein the guide rail of the articular trial includes a second hook to engage with the plurality of rails of the spacer to restrict inferior and superior movement between the articular trial and the spacer.

14. The tibial trial of claim 11, wherein the guide rail of the articular trial includes a first hook to engage with a second hook of the plurality of rails of the spacer to restrict inferior and superior movement between the articular trial and the spacer.

15. The tibial trial of claim 11, wherein after the guide rail of the articular trial is engaged with the plurality of rails of the spacer, the combined spacer and articular trial is lifted from the tibial tray and then moved anteriorly out from between the tibial tray and the femoral trial or the femoral implant.

16. A tibial trial comprising:
a tibial tray having a perimeter, the tibial tray comprising a rim extending about a substantial portion of the perimeter;
a spacer with a superior side and an inferior side, wherein the inferior side defines a periphery sized and shaped to contact the rim located on the tibial tray to restrict motion of the spacer relative to the tibial tray when connected to the tibial tray, the spacer comprising a first interlocking mechanism extending superiorly therefrom, the first interlocking mechanism including medial and lateral sidewalls and a plurality of rails extending laterally from the medial and lateral sidewalls of the first interlocking mechanism, the plurality of rails extending in an anterior to posterior direction, the plurality of rails defining a groove along the medial and lateral sidewalls of the first interlocking mechanism;
an articular trial with an inferior side and with a superior side configured to interact with a femoral trial or a femoral implant, the articular trial being configured to be slid in an anterior to posterior direction between the spacer and the femoral trial or the femoral implant, the articular trial comprising a recess formed in the inferior surface thereof, the recess arranged and configured to receive the first interlocking mechanism, the articular trial further including a plurality of guide rails extending laterally into the recess, the plurality of guide rails extending in an anterior to posterior direction; and
wherein when the articular trial is slid in an anterior to posterior direction between the spacer and the femoral trial or the femoral implant, the plurality of guide rails on the articular trial interlock with the grooves defined by the plurality of rails extending from the medial and lateral sidewalls of the first interlocking mechanism of the spacer without moving the femoral trial or femoral implant superiorly relative to the spacer.

17. The tibial trial of claim 16, wherein the articular trial includes a post configured to be received within a recess in the femoral trial or the femoral implant.

18. The tibial trial of claim 16, wherein the articular trial includes a raised portion extending from the inferior side of the trial and located on an anterior portion of the articular trial, wherein when the articular trial is slid in an anterior to posterior direction relative to the spacer, the raised portion of the articular trial contacts the superior side of the spacer such that anterior movement between the articular trial and the spacer is stopped at a predefined limit.

19. The tibial trial of claim 16, wherein the tibial tray includes a ridge across a superior portion of the tibial tray.

20. A tibial trial comprising:
a tibial tray having a superior portion, the tibial tray comprising a ridge extending across the superior portion;
a spacer with a superior side and an inferior side, wherein the inferior side is sized and shaped to connect with the ridge extending across the superior portion of the tibial tray to restrict motion of the spacer relative to the tibial tray when connected to the tibial tray, the spacer comprising a first interlocking mechanism extending superiorly therefrom, the first interlocking mechanism including medial and lateral sidewalls and a plurality of rails extending laterally from the medial and lateral sidewalls of the first interlocking mechanism, the plurality of rails extending in an anterior to posterior direction, the plurality of rails defining a groove along the medial and lateral sidewalls of the first interlocking mechanism, the spacer further comprising a first stop within the groove and located at a posterior portion of the groove;
an articular trial with an inferior side and with a superior side configured to interact with a femoral trial or a femoral implant, the articular trial being configured to be slid in an anterior to posterior direction between the spacer and the femoral trial or the femoral implant, the articular trial comprising a recess formed in the inferior surface thereof, the recess arranged and configured to receive the first interlocking mechanism, the articular trial further including a plurality of guide rails extending laterally into the recess, the plurality of guide rails extending in an anterior to posterior direction, the articular trial further comprising a second stop oblique to the guide rail; and
wherein when the articular trial is slid in an anterior to posterior direction between the spacer and the femoral trial or the femoral implant, the plurality of guide rails of the articular trial interlock with the grooves defined by the plurality of rails extending from the medial and lateral sidewalls of the first interlocking mechanism of the spacer without moving the femoral trial or femoral implant superiorly relative to the spacer and the second stop is engageable with the first stop to limit movement of the articular trial relative to the spacer along the groove.

\* \* \* \* \*